United States Patent [19]

Beck

[11] Patent Number: 5,242,691
[45] Date of Patent: * Sep. 7, 1993

[54] ANTI-INFLAMMATORY FACTOR, METHOD OF ISOLATION, AND USE

[75] Inventor: Lee R. Beck, Lebanon, Ohio

[73] Assignee: Stolle Research & Development Corporation, Cincinnati, Ohio

[*] Notice: The portion of the term of this patent subsequent to Sep. 11, 2007 has been disclaimed.

[21] Appl. No.: 580,382

[22] Filed: Sep. 11, 1990

Related U.S. Application Data

[60] Division of Ser. No. 910,297, Sept. 17, 1986, Pat. No. 4,919,929, and Ser. No. 546,162, Oct. 27, 1983, Pat. No. 4,636,384, and a continuation-in-part of Ser. No. 177,223, Apr. 4, 1988, Pat. No. 4,956,349, which is a continuation-in-part of Ser. No. 1,848, Jan. 9, 1987, Pat. No. 4,897,265, which is a continuation-in-part of Ser. No. 384,625, Jun. 3, 1982, abandoned, said Ser. No. 910,297, Pat. No. 4,919,929, is a continuation of Ser. No. 576,001, Feb. 1, 1983, abandoned.

[51] Int. Cl.⁵ .............................................. A61K 35/20
[52] U.S. Cl. ................................... 424/535; 424/85.8
[58] Field of Search .............................. 424/535, 85.8

[56] References Cited

U.S. PATENT DOCUMENTS

| | | | |
|---|---|---|---|
| 3,128,230 | 4/1964 | Heinbach | 167/78 |
| 3,376,198 | 4/1968 | Petersen et al. | 167/78 |
| 4,284,623 | 8/1981 | Beck | 424/85 |
| 4,324,782 | 4/1982 | Beck | 424/87 |
| 4,636,384 | 1/1987 | Stolle et al. | 424/87 |
| 4,732,757 | 3/1988 | Stolle et al. | 424/87 |
| 4,897,265 | 1/1990 | Stolle et al. | 424/87 |
| 4,956,349 | 9/1990 | Beck | 514/54 |

FOREIGN PATENT DOCUMENTS

| | | |
|---|---|---|
| 0064103 | 11/1982 | European Pat. Off. |
| 0300102 | 1/1989 | European Pat. Off. |
| 0336694 | 10/1989 | European Pat. Off. |
| WO89/09602 | 10/1989 | PCT Int'l Appl. |
| 1211876 | 11/1970 | United Kingdom |
| 1442283 | 7/1976 | United Kingdom |

OTHER PUBLICATIONS

Owens, W. E. et al., *Proc. Soc. Exp. Biol. Med.*, 90:79 (1989).

*Primary Examiner*—Douglas W. Robinson
*Assistant Examiner*—Jean C. Witz
*Attorney, Agent, or Firm*—Sterne, Kessler, Goldstein & Fox

[57] ABSTRACT

The invention relates to a substantially pure anti-inflammatory factor isolated from milk collected from a milk producing animal, to the purification, identification, and characterization of said factor, and to a method for treating inflammation in an animal which comprises administering to the animal an anti-inflammatorily effective amount of the anti-inflammatory factor. In a preferred embodiment, the factor is isolated from milk is produced by a milk producing animal maintained in a hyperimmunized state.

25 Claims, 25 Drawing Sheets

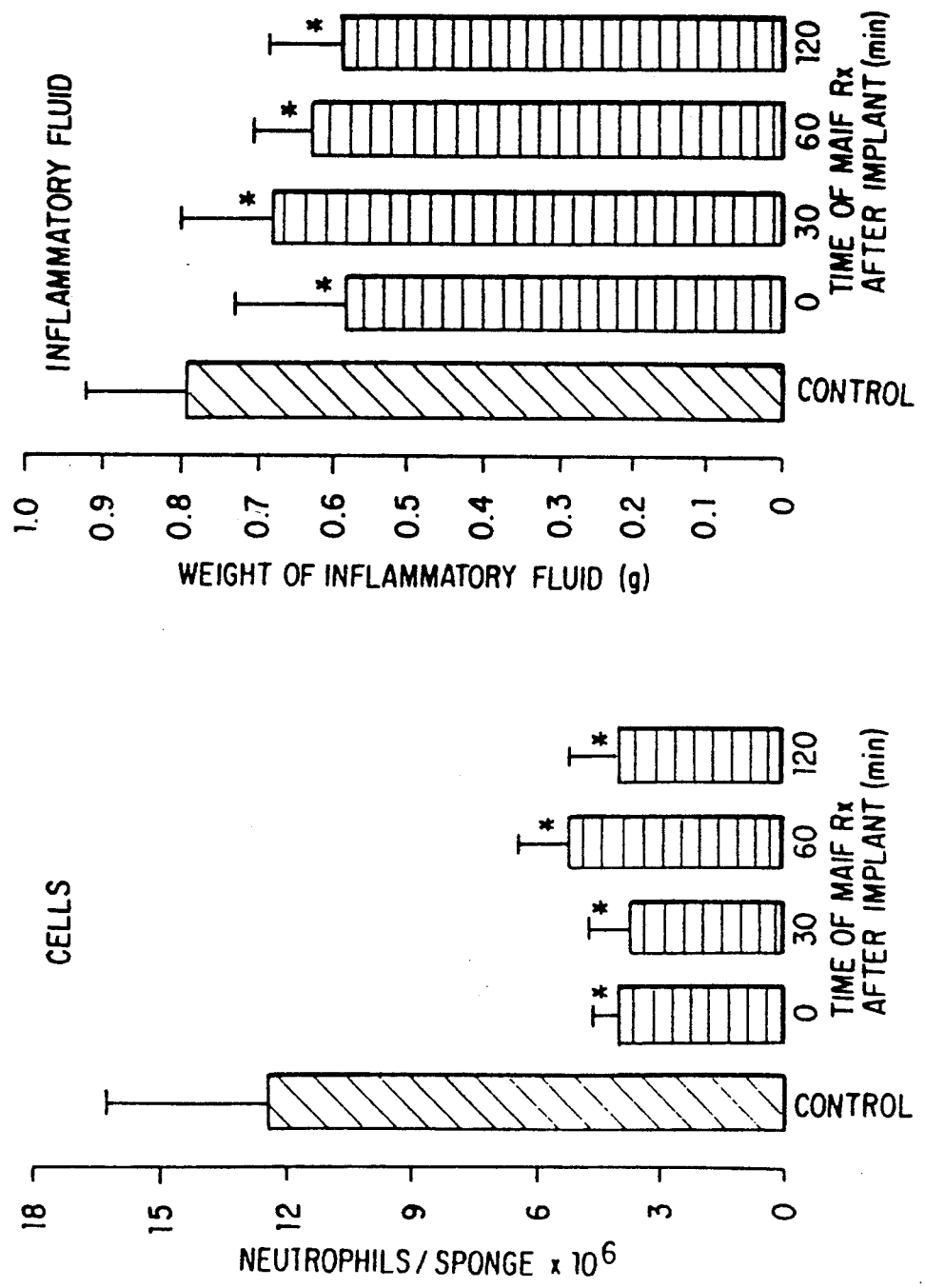

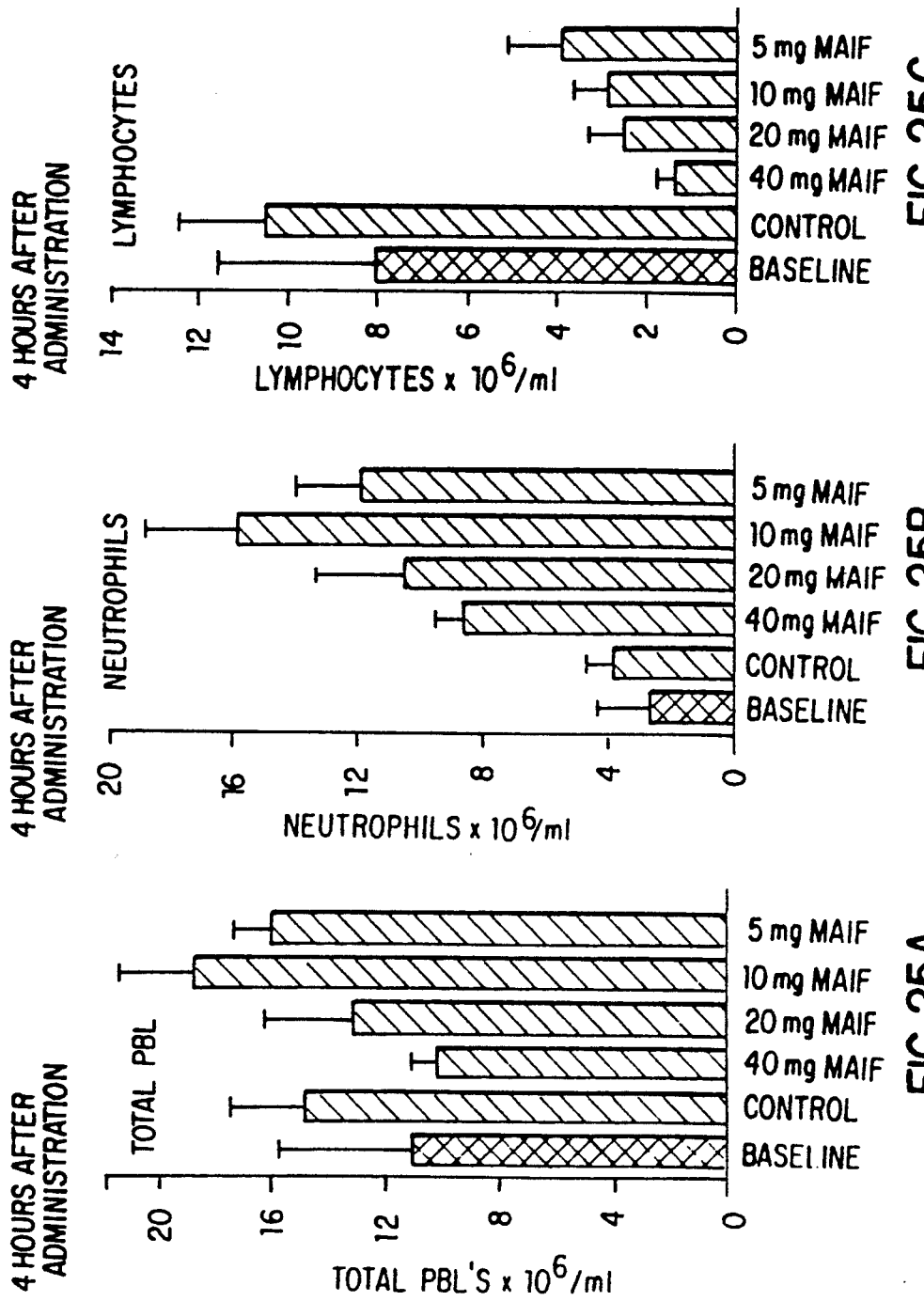

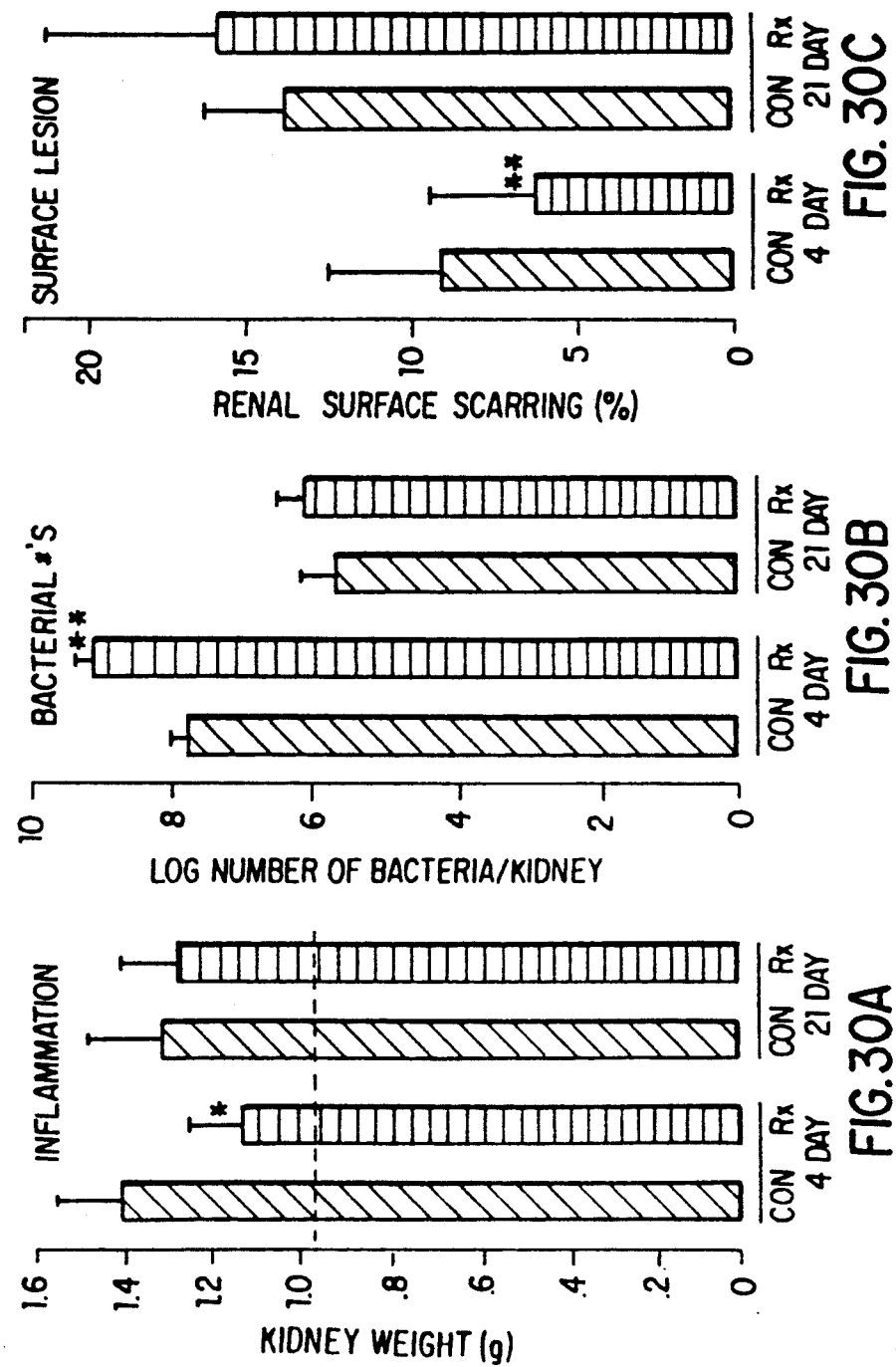

ANTI-INFLAMMATORY FACTOR, METHOD OF ISOLATION, AND USE

This application is a continuation-in-part of Ser. No. 177,223, now U.S. Pat No. 4,956,349, filed Apr. 4, 1988, which is a continuation-in-part of Ser. No. 001,848, now U.S. Pat. No. 4,897,265, filed Jan. 9, 1987, which is a continuation-in-part of U.S. Ser. No. 384,625; filed Jun. 3, 1982, now abandoned, and a division of Ser. No. 546,162, now U.S. Pat. No. 4,636,384, filed Oct. 27, 1983, and of U.S. Ser. No. 910,297, filed Sep. 17, 1986, now U.S. Pat. No. 4,919,929, which is a file wrapper continuation of U.S. Ser. No. 576,001, filed Feb. 1, 1983, now abandoned, all of which are fully incorporated herein by reference.

BACKGROUND OF THE INVENTION

1. Field of the Invention

The present invention relates to an anti-inflammatory factor, a process for its production in substantially pure form, and a method for its use in the treatment of inflammation.

2. Description of the Background Art

Inflammation, as defined in Dorland's Medical Dictionary, is "a localized protective response elicited by injury or destruction of tissues which serves to destroy, dilute or wall off both the injurious agent and the injured tissue." It is characterized by fenestration of the microvasculature, leakages of the elements of blood into the interstitial spaces, and migration of leukocytes into the inflamed tissue. On a macroscopic level, this is usually accompanied by the familiar clinical signs of erythema, edema, tenderness (hyperalgesia) and pain. During this complex response, chemical mediators such as histamine, 5-hydroxytryptamine, various chemotactic factors, brakykinin, leukotrienes, and prostaglandins are liberated locally. Phagocytic cells migrate into the area, and cellular lysosomal membranes may be ruptured, releasing lytic enzymes. All of these events may contribute to the inflammatory response.

Inflammation in patients with rheumatoid arthritis probably involves the combination of an antigen (gamma globulin) with an antibody (rheumatoid factor) and complement causing the local release of chemotactic factors that attract leukocytes. The leukocytes phagocytose the complexes of antigen-antibody and complement and also release the many enzymes contained in their lysosomes. These lysosomal enzymes then cause injury to cartilage and other tissues, and this furthers the degree of inflammation. Cell-mediated immune reactions may also be involved. Prostaglandins are also released during this process.

Prostaglandins, which are likely to be generated in inflammation, cause erythema and increase local blood flow. Two important vascular effects of prostaglandins are not generally shared by other mediators of inflammation—a longlasting vasodilator action and a capacity to counteract the vasoconstrictor effects of substances such as norepinephrine and angiotensin.

A number of mediator of inflammation increase vascular permeability (leakage) in the post-capillary and collecting venules. In addition, migration of leukocytes into an inflamed area is an important aspect of the inflammatory process.

The Arthus reaction is an inflammatory response brought about by the formation of immune complexes at subcutaneous sites where an antigen complexes with antibody to that antigen. Neutrophils characteristically attach to the Fc portion of the immunoglobulin complex that forms at the subcutaneous injection site where they release digestive enzymes, causing visible acute inflammation. Thus the reaction is primarily neutrophil-mediated and agents that effect the development of the reaction do so via an effect on these cells.

There are several pathways whereby an agent might interfere with neutrophil migration from the blood vessels to an inflammatory site. One likely pathway is the inhibition of margination, the reversible "sticking" of inflammatory cells to the endothelial cell lining of the blood vessel wall. In the normal state about 50% of neutrophils are reversibly adhered, but during an acute inflammatory response, adhesion becomes much stronger and is a key step in the process of neutrophil migration. While prostaglandins are unlikely to be directly involved in the chemotactic response, another product of the metabolism of arachidonic acid, leukotriene, is a very potent chemotactic substance.

The anti-inflammatory response is any response characterized by inflammation as defined above. It is well known to those skilled in the medical arts that the inflammatory response causes much of the physical discomfort, i.e., pain and loss of function, that has come to be associated with different diseases and injuries. Accordingly, it is a common medical practice to administer pharmacological agents which have the effect of neutralizing the inflammatory response. Agents having these properties are classified as anti-inflammatory drugs. Anti-inflammatory drugs are used for the treatment of a wide spectrum of disorders, and the same drugs are often used to treat different diseases. Treatment with anti-inflammatory drugs is not for the disease, but most often for the symptom, i.e., inflammation.

The anti-inflammatory, analgesic, and anti-pyretic drugs are a heterogeneous group of compounds, often chemically unrelated, which nevertheless share certain therapeutic actions and side-effects. Corticosteroids represent the most widely used class of compounds for the treatment of the anti-inflammatory response. Proteolytic enzymes represent another class of compounds which are thought to have anti-inflammatory effects. Hormones which directly or indirectly cause the adrenal cortex to produce and secrete steroids represent another class of anti-inflammatory compounds. A number of non-hormonal anti-inflammatory agents have been described. Among these, the most widely used are the salicylates. Acetylsalicylic acid, or aspirin, is the most widely prescribed analgesic-antipyretic and anti-inflammatory agent. Examples of steroidal and non-steroidal anti-inflammatory agents are listed in the *Physician's Desk Reference*, 1987 (see pp. 207 and 208 for an index of such preparations).

The natural and synthetic corticosteroid preparations cause a number of severe side effects, including elevation of blood pressure, salt and water retention, and increased potassium and calcium excretion. Moreover, corticosteroids may mask the signs of infection and enhance dissemination of infectious microorganisms. These hormones are not considered safe for use in pregnant women, and long-term corticosteroid treatment has been associated with gastric hyperactivity and/or peptic ulcers. Treatment with these compounds may also aggravate diabetes mellitus, requiring higher doses of insulin, and may produce psychotic disorders. Hormonal anti-inflammatory agents which indirectly increase the production of endogenous corticosteroids have the same potential for adverse side-effects.

The non-hormonal anti-inflammatory agents are synthetic biochemical compounds which can be toxic at high doses with a wide spectrum of undesirable side-effects. For example, salicylates contribute to the serious acid-base balance disturbances that characterize poisoning by this class of compounds. Salicylates stimulate respiration directly and indirectly. Toxic doses of salicylates cause central respiratory paralysis as well as circulatory collapse secondary to vasomotor depression. The ingestion of salicylate may result in epigastric distress, nausea, and vomiting. Salicylate-induced gastric bleeding is well known. Salicylates can produce hepatic injury, and lead to a prolongation of clotting time. Therefore, aspirin should be avoided in patients with severe hepatic damage, hypoprothrombinemia, vitamin K deficiency, or hemophilia, because the inhibition of platelet hemostatis by salicylates can result in hemorrhage. Salicylate intoxication is common, and over 10,000 cases of serious salicylate intoxication are seen in the United States every year, some of them being fatal, and many occurring in children. See Goodman and Gilman's *The Pharmacological Basis of Therapeutics*, 7th Ed., 1985. Accordingly, in spite of the large number of anti-inflammatory agents that are currently available, there still exists a need for a safe, effective anti-inflammatory product which is free of side-effects and adverse reactions.

If a natural food product, such as one derived from milk, for example, could be obtained having anti-inflammatory effects, it would be an easily administrable, readily available, safe therapeutic composition.

It has been known in the prior art to produce milks having a variety of therapeutic effects. Beck, for example, has disclosed a milk containing antibody to *Streptococcus mutans* that has dental caries inhibiting effect (U.S. Pat. No. 4,324,782). The milk is obtained by immunizing a cow with *S. mutans* antigen in two stages and obtaining the therapeutic milk therefrom.

Stolle et al. have disclosed a method for treating vascular disorders or pulmonary disorders associated with smoking in an animal which comprises administering to the animal milk collected from a cow being maintained in a hyperimmune state (U.S. Pat. No. 4,636,384). Beck has disclosed a method for treating inflammation in an animal which comprises administering to the animal an anti-inflammatory effective amount of milk collected from a cow maintained in an anti-inflammatory factor producing state (U.S. Pat. No. 4,284,623). Heinbach, U.S. Pat. No. 3,128,230, has described milk containing globulins of alpha, beta, and gamma components by inoculating a cow with antigenic mixtures. Peterson et al. (U.S. Pat. No. 3,376,198), Holm (U.S. application (published) Ser. No. 628,987), Tunnah et al. (British Patent No. 1,211,876) and Biokema S.A. (British Patent 1,442,283) have also described antibody-containing milks.

None of the aforementioned references, however, disclose the identity of the component or components of therapeutic milks which produce the desired therapeutic effects. For example, in Beck, U.S. Pat. No. 4,284,623, the milk products used as a therapeutic means consist of either fluid whole milk, fluid fat-free whey, or whole milk powders. Although each of these milk products has anti-inflammatory properties, the factor or factors that actually provide the therapeutic benefits have not yet been isolated or identified.

SUMMARY OF THE INVENTION

The present invention is based upon the inventors' consideration that an isolated and purified anti-inflammatory milk product would be most useful to treat anti-inflammatory disorders in an animal.

With this in mind, the present inventors isolated and partially purified and characterized an anti-inflammatory factor from hyperimmune bovid milk, hereinafter called milk anti-inflammatory factor (MAIF).

Accordingly, the present invention includes the purified milk anti-inflammatory factor, isolated from milk from milkproducing animals previously hyperimmunized against particular polyvalent antigens. It is effective against inflammatory conditions when isolated, purified, and administered in an amount and under a regimen sufficient to product anti-inflammatory effects. The isolation of the active factor from milk of hyperimmunized bovines led to the unexpected finding that MAIF occurs in small quantities in the milk of normal bovines. This discovery had been hidden by the fact that the concentration of MAIF in normal bovine milk is too low to confer discernible anti-inflammatory properties to the milk. The MAIF of normal milk can, however, be concentrated by the isolation process of the invention, and thereafter can be used effectively to treat inflammation.

The present invention further includes the use of purified MAIF as a means of blocking the cellular inflammatory response by administering a blocking dose of hyperimmune milk factor to an animal in which the blocking dose is sufficient to effectively block the cellular inflammatory response. The blocking dose is sufficient to inhibit the migration of inflammatory cells particularly where the inflammatory cells are neutrophils. The MAIF is also used to inhibit the inflammatory response that occurs during the Arthus reaction. The MAIF can also be used to inhibit the cellular inflammatory response that results from infection of an animal. MAIF can also be used as a means of blocking the cellular inflammatory response that results from acute phase reactant release. MAIF can also be used to inhibit cytokine action in an animal by administering an effective blocking dose of hyperimmune milk factor to the animal. The inhibition of cytokine action above is at the receptor of an inflammatory cell. The MAIF may also be used to prevent the adhesion of neutrophils to endothelial cells. The use comprises administration of a blocking dose of MAIF to an animal wherein the blocking dose is sufficient to effectively prevent the adhesion. MAIF is advantageously administered intravenously.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 22. Effect of MAIF, administered at a dose of 20 mg per rat, to inhibit the ability of inflammatory cells to accumulate in subcutaneously implanted sponges when administered at the time of implant or up to 120 minutes after implant. *=p<0.01.

FIG. 25. Dose-response relationship between i.v. MAIF administration and circulating leukocyte numbers (<0.01).

FIG. 30. Effect of 40 mg of MAIF, given intravenously at the time of challenge and 48 hours later, on the pathogenesis of experimental pyelonephritis. The dotted line on the left-hand graph represents the mean background kidney weight. *=p<0.01; **=p<0.02.

DETAILED DESCRIPTION OF THE PREFERRED EMBODIMENTS

Figure 1:
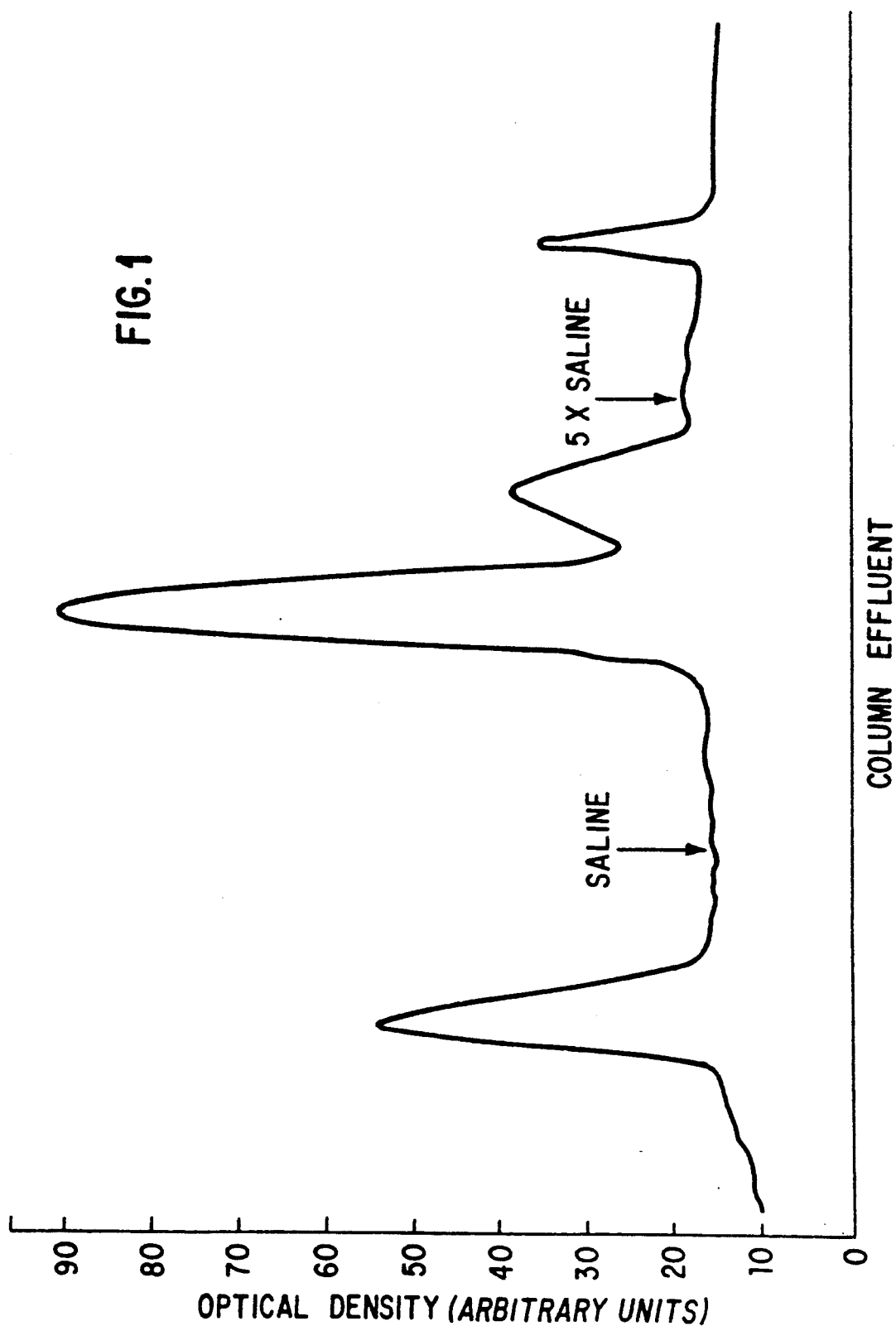
FIG. 1. Isolation of MAIF by ion-exchange chromatography on a column of DEAE-cellulose, in Step 2 of the preferred process.

The invention comprises the isolation and purification of MAIF and the administration of said MAIF to an animal for the purpose of treating anti-inflammatory disorders.

By the term "milk anti-inflammatory factor" is intended a factor obtained from either hyperimmune milk or normal cow's milk. By the term "substantially pure milk anti-inflammatory factor" is intended, for the purpose of this invention, an anti-inflammatory factor that elutes as a single major symmetrical peak on HPLC chromatography, after removal of high molecular weight substances (>10,000 daltons) and isolation of the low molecular weight, negatively-charged species by ion-exchange chromatography. Both normal milk and hyperimmune milk can be processed by the methods described herein to obtain the MAIF.

By the term "hyperimmune milk" is intended, for the purpose of this invention, milk obtained from milk-producing animals maintained in a hyperimmune state, the details for hyperimmunization being described in greater detail below.

By the term "whey" is intended, for the purpose of this invention, milk from which cream has been removed.

By the term "normal milk" is intended for the purpose of the invention milk that is obtained from milk-producing animals by conventional means and dairy practices.

By the term "milk-producing animal" is intended, for the purpose of this invention, mammals that produce milk in commercially feasible quantities, preferably cows, sheep and goats, more preferably dairy cows of the genus Bos (bovid), particularly those breeds giving the highest yields of milk, such as Holstein.

By the term "bacterial antigen" is intended, for the purpose of this invention, a lyophilized preparation of heatkilled bacterial cells.

By the term "microencapsulated form" is intended, for the purpose of this invention, polymeric microparticles encapsulating one or more bacterial antigens for administration to milk-producing animals.

By the term "inflammation" is intended, for the purpose of this invention, a localized protective response elicited by injury or destruction of tissues which serves to destroy, dilute or wall off both the injurious agent and the injured tissue, characterized in the acute form by the classical sequence of pain, heat, redness, swelling, and loss of function, and histologically involving a complex series of events, including dilatation of the arterioles, capillaries, and venules with increased permeability and blood flow, exudation of fluids including plasma proteins, and leukocyte migration into the inflammatory focus.

By the term "treating" is intended, for the purposes of this invention, that the symptoms of the disorder and/or pathogenic origin of the disorder be ameliorated or completely eliminated.

By the term "administer" is intended, for the purpose of this invention, any method of treating a subject with a substance, such as orally, intranasally, parenterally (intravenously, intramuscularly, or subcutaneously), or rectally.

By the term "animal" is intended, for the purpose of this invention, any living creature that is subject to inflammation, including humans, farm animals, domestic animals, or zoological garden animals.

Examples of inflammatory conditions that may be treated by the isolated and purified milk product of the present invention are conditions selected from the group consisting of acute and subacute bursitis, acute non-specific tendonitis, systemic lupus erythematosis, systemic dermatomyositis, acute rheumatic carditis, pemphigus, bullous dermatitis, herpeteformis, severe erythema, multiform exfoliative dermatitis, cirrhosis, seasonal perennial rhinitis, bronchial asthma, ectopic dermatitis, serum sickness, keratitis, opthalmicus iritis, diffuse ureitis, choriditis, optic neuritis, sympathetic opthalmia, symptomatic sarcoidosis, Loeffler's syndrome, berylliosis, hemolytic anemia, mastitis, mastoiditis, contact dermatitis, allergic conjunctivitis, psoriatic arthritis, ankylosing spondylitis, acute gouty arthritis, and herpes zoster. Further, the isolated and purified milk product may be used to treat individuals who are exposed to potentially inflammatory agents.

The invention is based in part on the discovery that when a milk-producing animal such as a bovid is brought to a specific state of hyperimmunization, the animal will produce milk which has supranormal levels of the highly beneficial MAIF, said MAIF not only suppressing the symptoms of inflammation in man and other animals, but also being a prophylactic agent in anticipation of the presence of inflammatory agents in the recipient. By the term "supranormal levels" is intended levels in excess of that found in milk from non-hyperimmunized animals. The induction of immune sensitivity alone is insufficient to cause the appearance of supranormal levels of MAIF in milk, as is shown by the fact that normal cow's milk does not contain these supranormal levels, even though the cows have become sensitized against various antigens during normal immunization against cow diseases and during normal exposure to the environment. It is only in specific hyperimmune states that the milk has the desired supranormal levels.

This special state may be achieved by administering an initial immunization, followed by periodic boosters with sufficiently high doses of specific antigens. The preferred dosage of booster should be equal to or greater than 50% of the dosage necessary to produce primary immunization of the bovid. Thus, there is a threshold booster dosage below which the properties are not produced in the milk, even though the cow is in what normally would be called an immune state. In order to achieve the requisite hyperimmune state, it is essential to test the hyperimmune milk after a first series of booster administrations. If the beneficial factors are not present in the milk, additional boosters of high dosage are administered until the properties appear in the milk.

The process of producing the hyperimmune milk containing supranormal levels of MAIF is disclosed in co-pending U.S. Ser. No. 069,139, filed Jul. 2, 1987, and in co-pending U.S. Ser. No. 910,297, filed Sep. 17, 1986, a file wrapper continuation of U.S. patent application Ser. No. 576,001, filed Feb. 1, 1983, which are incorporated herein by reference in their entirety. In summary, one process of producing the hyperimmune milk containing supranormal levels of MAIF comprises the following steps: (1) antigen selection; (2) primary immunization of the bovid; (3) testing the serum to confirm sensitivity induction; (4) hyperimmunization with boosters of appropriate dosage; and, optionally, (5) testing the milk for anti-inflammatory properties; (6) collecting the milk from the hyperimmune bovid; and (7) processing the milk to isolate the MAIF.

Step 1: Any antigens or combination of antigens may be employed. The antigens can be bacterial, viral, protozoan, fungal, cellular, or any other substances to which the immune system of a milk-producing animal will respond. The critical point in this step is that the antigen(s) must be capable, not only of inducing immune and hyperimmune states in the milkproducing animal, but also of producing supranormal levels of MAIF in the milk. Any antigen can be used to produce supranormal levels of MAIF. One preferred vaccine is a mixture of polyvalent bacterial antigens, referred to as Series 100 vaccine, described in detail in Example 1A below.

Step 2: The antigen(s) can be administered in any method that causes sensitization. In one method, a vaccine composed of antigen derived from $1 \times 10^6$ to $1 \times 10^{20}$, preferably $10^8$ to $10^{10}$, most preferably $2 \times 10^8$, heat-killed bacteria is administered by intramuscular injection. However, other methods such as intravenous injection, intraperitoneal injection, rectal suppository, or oral administration may be used.

Step 3: It is necessary to determine whether or not the milk-producing animal has become sensitive to the antigen. There are a number of methods known to those skilled in the art of immunology to test for sensitivity (Methods in Immunology and Immunochemistry, William, C. A., and Chase, W. M., Academic Press, N.Y., vols. 1-5 (1975)). The preferred method is to use a polyvalent vaccine comprising multiple bacterial species as the antigen and to test for the presence of agglutinating antibodies in the serum of the animal before and after challenge with the vaccine. The appearance of milk antibodies after immunization with the vaccine indicates sensitivity; at this point it is possible to proceed to step 4.

Step 4: This involves the induction and maintenance of the hyperimmune state in the sensitized animal. This is accomplished by repeated booster administration at fixed time intervals of the same polyvalent vaccine that was used to achieve the primary sensitization. A two-week booster interval is optimal for polyvalent bacterial antigens. However, it is necessary to ensure that the animal does not pass from a hyperimmune state to a state of immune tolerance to the antigen.

In a preferred embodiment, hyperimmunization of bovids may be achieved by a single administration of microencapsulated vaccine, prepared as described in detail in Example 1B below. The advantage of the controlled release form of hyperimmunization is that the constant exposure to the antigen ensures that the animal remains in the hyperimmune state.

In an alternative embodiment, it is also possible to combine different immunization procedures, e.g., simultaneously administering microencapsulated and liquid antigen, or intramuscular injection for primary immunization, and booster doses by oral administration or parenteral administration by microencapsulation means. Many different combinations of primary and hyperimmunization are known to those skilled in the art.

Step 5: It is necessary to test the milk for anti-inflammatory activity levels. This can be accomplished by any research technique that tests the effects of either the hyperimmune milk or products derived therefrom upon inflammation. Chemical-induced inflammation of the rat paw is a standard assay for anti-inflammatory drugs.

Step 6: This involves the collection and processing of the milk. The milk can be collected by conventional methods. Processing the milk to isolate the MAIF is described below.

The simplest process for isolating, purifying and testing the MAIF comprises the following steps:

1. defatting the hyperimmune milk to produce skim milk;
2. removing casein from skim milk to produce whey;
3. removal from the whey macromolecules of molecular weight greater than about 10,000 dalts by ultrafiltration;
4. fractionating the product from step 3 using an ionexchange resin column to isolate a negatively-charged MAIF species of molecular weight less than about 10,000 daltons;
5. separating the negatively-charged species from step 4 by molecular sieve chromatography; and
6. biological assay of MAIF from step 5.

In an alternative preferred embodiment, the fractions from molecular sieve chromatography that have biological activity are further purified by filtration through a membrane that remains macromolecules of molecular weight greater than about 5000 daltons.

7. The anti-inflammatory action of the milk factor is tested on edema that is caused by the injection of a solution of carrageenan into the paw of rats. The rat paw test is the standard animal test for anti-inflammatory drugs. Winter, C. A., Risley, G. A., Nuss, A. W., "Carrageenan-Induced Edema in the Hind Paw of the Rat as an Assay for Anti-inflammatory Drugs," *Proc. Soc. Exper. Biol. Med.* 3:544 (1967). A variety of other tests may be used. Wetnick, A. S., and Sabin, C., "The Effects of Clonixin and Bethaurethasone on Adjuvant-Induced Arthritis and Experimental Allergic Encephalomyelitis in Rats," *Jap. J. Pharm.* 22:741 (1972). However, the rat paw test is the most simple and direct test available, and has been show to be satisfactory for all anti-inflammatory drugs. This test has been described in detail in Beck, U.S. Pat. No. 4,284,623, which is incorporated herein by reference to the extent that it describes the rat paw test. Briefly, the test involves the injection of a small quantity of carrageenan into the footpad of adult white rats. This is known to induce an inflammatory response. The resulting degree of swelling can be quantified. Samples containing an anti-inflammatory factor are administered to the rat by a suitable route, preferably by intraperitoneal injection, and the blockade or amelioration of the inflammatory process quantified by either volumetric or gravimetric methods.

In summary, one can isolate the anti-inflammatory factor from hyperimmunized milk by following a process of defatting the milk, removing casesin, removing macromolecules of greater than 10,000 daltons, and continuing with ion exchange and molecular sieve chromatography. The bioligical activity of appropriate preparations of anti-inflammatory factor can be tested by doing a dose-response experiment on rats as described herein.

The compositions of the present invention may be administered by any means that provide anti-inflammatory activity. For example, administration may be parenteral, subcutaneous, intravenous, intramuscular, intraperitoneal or oral.

Solid dosage forms for oral administration include capsules, tablets, pills, powders and granules. In such solid dosage forms the active compound is admixed with at least one inert diluent such as sucrose, lactose or starch. Such dosage forms can also comprise, as is normal practice, additional substances other than inert diluent. In the case of capsules, tablets, and pills, the dosage forms may also comprise buffering agents. Tablets and pills can additionally be prepared with an enteric coating.

Liquid dosage forms for oral administration include pharmaceutically acceptable emulsion, solutions, suspensions, syrups and elixirs containing inert diluents commonly used in the pharmaceutical art. Besides inert diluents, such compositions can also include adjuvants, such as wetting agents, emulsifying and suspending agents, and sweetening.

Preparations according to this invention for parenteral administration include sterile aqueous or nonaqueous solutions, suspensions or emulsions. Examples of nonaqueous solvents or vehicles are propylene glycol, polyethylene glycol, vegetable oils such as olive oil and injectable organic esters such as ethyl oleate.

The dosage of active ingredients in the composition of this invention may be varied; however it is necessary that the amount of the active ingredient shall be such that a suitable dosage form is obtained. The selected dosage form depends upon the desired therapeutic effect, on the route of the administration and on the duration of the treatment.

Administration dosage and frequency will depend on the age and general health condition of the patient, taking into consideration the possibility of side effects. Administration will also be dependent on concurrent treatment with other drugs and patients tolerance of the administered drug.

The invention is based in part upon the unexpected discovery that a MAIF can be isolated and purified and is effective in treating a variety of inflammatory processes in humans and animals. In a preferred embodiment, the MAIF is produced by hyperimmunizing a milk-producing animal against a bacterial antigen vaccine. The vaccine used to hyperimmunize the animals does not contain anti-inflammatory activity. It is surprising, therefore, that treatment with an isolated and purified factor, obtained from animals immunized against a mixed bacterial antigen vaccine, is effective in alleviating or eliminating inflammatory processes.

Having now described the invention in general terms, the same will be further described by reference to certain specific examples that are provided herein for purposes of explanation only, and are not intended to be limiting unless otherwise specified.

EXAMPLE 1A

Preparation of S-100 Vaccine

A bacterial culture containing the spectrum of bacteria shown in Table 1 below as obtained from the American Type Culture Collection was reconstituted with 15 ml of media and incubated over night at 37° C. Once good growth was obtained, approximately one-half of the bacterial suspension was employed to inoculate one liter of broth with the inoculate being incubated at 37° C. The remaining suspension was transferred to sterile glycol tubes and stored at −20° C. for up to six months.

After good growth was visible in the culture, the bacterial cells were harvested by centrifugation of the suspension for 20 minutes to remove the media. The bacterial pellet obtained was resuspended in sterile saline solution and the bacterial sample was centrifuged three times to wash the media from the cells. After the third sterile saline wash, the bacterial pellet obtained upon centrifugation was resuspended in a small amount of double distilled water.

The media-free bacterial suspension was heat-killed by placing the suspension in a glass flask in an 80° C. water bath overnight. The viability of the broth culture was tested with a small amount of heat-killed bacteria. Broth was inoculated with heat-killed bacteria, incubated at 37° C. for five days and checked daily for growth, as the bacteria have to be killed for use in the vaccine.

The heat-killed bacteria were lyophilized until dry. The dry bacteria were then mixed with sterile saline solution to a concentration of $2.2 \times 10^8$ bacterial cells/ml saline (1.0 optical density reading at 660 nm).

TABLE 1

S-100 Bacteria List

| Name | Media | Gram + or − | ATTC # |
|---|---|---|---|
| 1. Staph. aureus | BHI | + | 11631 |
| 2. Staph. epidermidis | BHI | + | 155 |
| 3. Strep. pyogenes, A. Type 1 | APT | + | 8671 |
| 4. Strep. pyogenes, A. Type 3 | APT | + | 10389 |
| 5. Strep. pyogenes, A. Type 5 | APT | + | 12347 |
| 6. Strep. pyogenes, A. Type 8 | APT | + | 12349 |
| 7. Strep. pyogenes, A. Type 12 | APT | + | 11434 |
| 8. Strep. pyogenes, A. Type 14 | APT | + | 12972 |
| 9. Strep. pyogenes, A. Type 18 | APT | + | 12357 |
| 10. Strep. pyogenes, A. Type 22 | APT | + | 10403 |
| 11. Aerobacter aerogenes | BHI | − | 884 |
| 12. Escherichia coli | BHI | − | 26 |
| 13. Salmonella enteritidis | BHI | − | 13076 |
| 14. Pseudomonas aeruginosa | BHI | − | 7700 |
| 15. Klebsiella pneumoniae | BHI | − | 9590 |
| 16. Salmonella typhimurium | BHI | − | 13311 |
| 17. Haemophilus influenzae | BHI | − | 9333 |
| 18. Strep. mitis | APT | + | 6249 |
| 19. Proteus vulgaris | BHI | − | 13315 |
| 20. Shigella dysenteriae | BHI | − | 11835 |
| 21. Diplococcus pneumoniae | APT | + | 6303 |
| 22. Propionibacter acnes | Broth | + | 11827 |
| 23. Strep. sanguis | APT | + | 10556 |
| 24. Strep. salivarius | APT | + | 13419 |
| 25. Strep. mutans | BHI | + | 25175 |
| 26. Strep. agalactiae | APT | + | 13813 |

Cows were given daily injections of 5 ml samples of the polyvalent liquid vaccine. Antibody (IgG) titer levels for the injected cattle were determined periodically by using an enzyme-linked immunoassay for bovine antibody against the polyvalent antigen.

EXAMPLE 1B

Immunization Procedures

Heat-killed bacteria were prepared in the manner described above. The polyvalent antigen sample (S-100) obtained was microencapsulated by a conventional phaseseparation process to prepare a polyvalent antigen-containing microparticle product. Generally, the antigen-containing shaped matrix materials are formed from polymers of biocompatible material, preferably biodegradable or bioerodable materials, preferably polylactic acid, polyglycolic acid, copolymers of lactic and glycolic acids, polycaptolactone, copolyoxalates, proteins such as collagen, fatty acid esters of glycerol, and cellulose esters. These polymers are well known in the art and are described, for example, in U.S. Pat. Nos. 3,773,919; 3,887,699; 4,118,470; 4,076,798; all incorporated by reference herein. The polymeric matrix material employed was a biodegradable lactide-glycolide copolymer.

Heat-killed bacterial antigens are encapsulated in such matrix materials, preferably as microspheres of between 1-500 microns diameter, preferably 10-250 microns. The encapsulation processes are conventional and comprise phase separation methods, interfacial reactions, and physical methods. Many combinations of matrices and many concentrations of assorted antigens may be employed, in order to provide for optimal rates of release of bacterial antigens to the host body from the microparticles. These combinations can be determined by those skilled in the art without undue experimentation.

The microparticles in the example were less than 250 microns in diameter. Approximately 750 mg of microparticles containing 22% (16.5 mg) of polyvalent antigen was then suspended in about 3 cc of a vehicle (1 wt % Tween 20 and 2 wt % carboxymethyl cellulose in water).

A small group of cattle was selected from a larger herd of cattle. Five of these randomly selected cattle were selected as controls. Four cattle were injected intramuscularly with microparticles containing polyvalent anigen. Microparticle samples were sterilized with 2.0 mRad of gamma radiation. Antibody (IgG) titer levels were determined periodically from samples of cows' milk obtained from the inoculated cows, as well as from the control cows.

EXAMPLE 2

Isolation of MAIF Factor from Hyperimmunized Milk

Step 1: Milk Filtrate Preparation

Twenty liters of fresh milk from hyperimmunized cows were run through a cream separator (DeLaval Model 102) to remove the fat.

The resulting sixteen liters of skimmed milk was ultrafiltered to remove the high molecular weight species (over 10,000 daltons) using a hollow fiber diafiltration/concentrator (Amicon DL-10L). The concentrator is equipped with two 10,000 daltons molecular weight cut-off cartridges (Amicon $H_5P_{10-43}$). The skimmed milk was run at the pump speed of 80 on the meter and inlet and outlet pressure of 30 psi and 25 respectively.

Twelve liters of the filtrate (<10,000 daltons) coming out of the cartridges at the flow rate of four liters per hour was frozen or lyophilized for storage and for further purification.

Step 2: Ion-Exchange Chromatography

The milk anti-inflammatory factor, MAIF, in the filtrate was first isolated by an anion exchange chromatography column.

In this procedure, DEAE-Sepharose CL-6B gel (Pharmacia) was used to pack a 5×10 cm glass column which was equilibrated with sterile double distilled water, pH 7.0.

One liter of filtrate (<10,000) was applied to the column and eluted with sterile double distilled water, pH 7.0 at the flow rate of 160 ml per hour. Ten milliliter fractions were collected and monitored at 280 nm in an LKB Uvicord 4700 absorptiometer with an optical density printed out on a connected recorder (Pharmacia REC-482).

The substances other than MAIF having positive and neutral charges are not bound to the DEAE-Sepharose gel. They are eluted at the fallthrough peak (first peak). The MAIF carrying a negative charge is retained by the gel.

To discharge the MAIF, the column was eluted with a stepwise gradient using sterile physiological saline, pH 7.0. A typical profile is shown in FIG. 1. Bioassay of the individual fractions revealed that the second peak contains the MAIF. Fractions comprising the second peak and its shoulder are used for further purification. Recovery studies show that 8.8 grams of dried powder were obtained by this process.

Step 3: Gel Filtration Chromatography

The second peak obtained from Step 2 contains MAIF and other negatively charged molecules; therefore, an additional refining step was needed. To achieve further purification, it is convenient to use a gel filtration column to separate various components on the basis of molecular weight.

In this process, Sephadex G-10 resin (Pharmacia) was packed into a 2.5×80 cm glass column and equilibrated with sterile double distilled water, pH 7.0. Two grams of the second fraction from Step 2 was redissolved in sterile double distilled water and applied to the top of the column. The column was eluted at the flow rate of 30 ml per hour. Fractions (3.3 ml) were collected and monitored at 254 nm and 280 nm (Pharmacia Duo Optical Unit) with optical density printed out on a connected recorder (Pharmacia REC-482).

Figure 2:
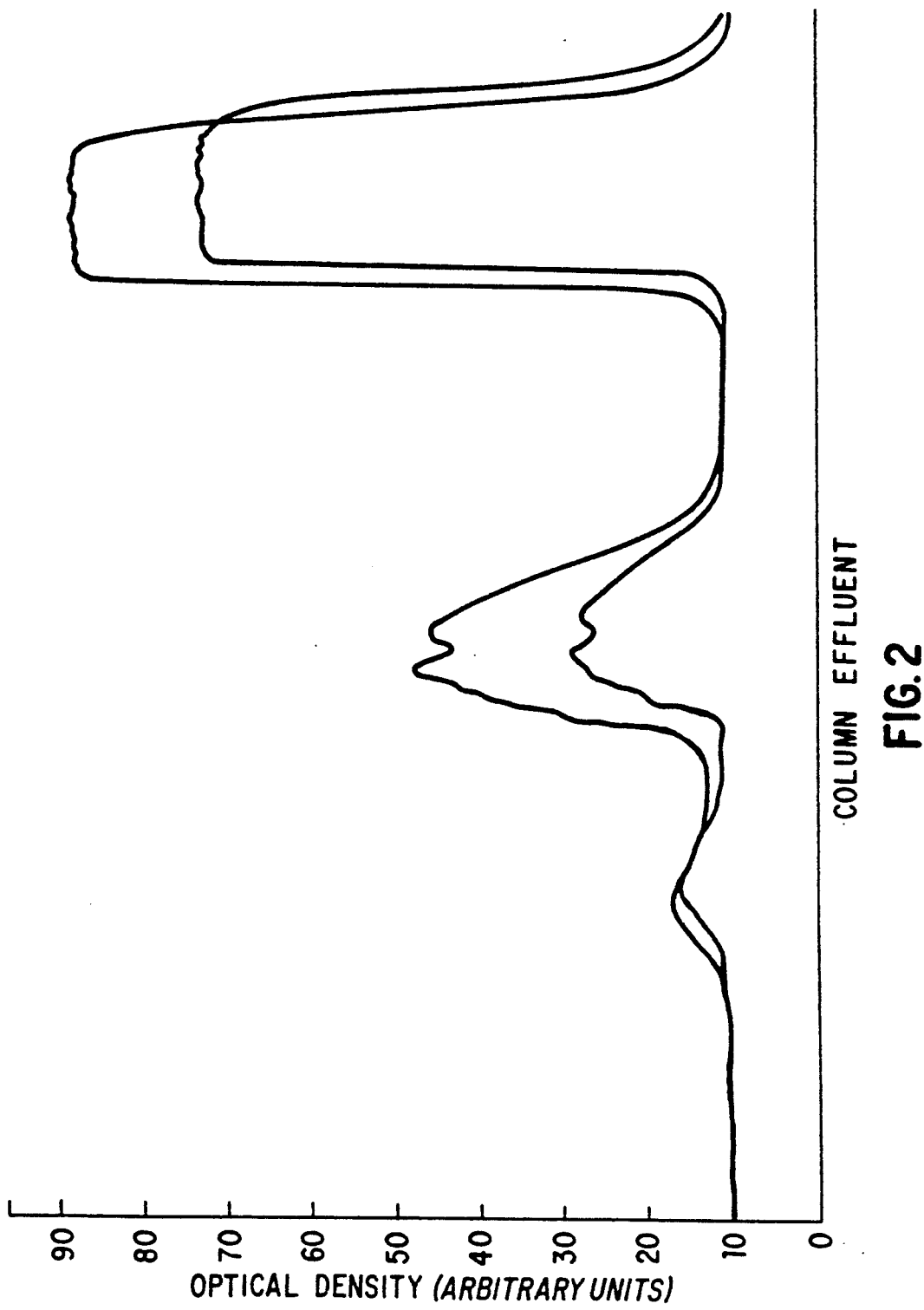
FIG. 2. Fractionation of the MAIF peak (second) from DEAE-cellulose chromatography (FIG. 1) on a Sephadex G-10 molecular sieve column, in step 3 of the preferred process.

Typically, there were 3 peaks shown in the elution profile as illustrated in FIG. 2. The first and second peaks contained MAIF activity.

The first peak is an aggregate that forms on the G-10 column which contains the active MAIF.

The second peak contains the nonaggregated form of the MAIF. Both the aggregate form (peak 1) and the nonaggregated form (peak 2) are biologically active in rat bioassay.

EXAMPLE 3

Characterization of Milk Anti-inflammatory Factor

The molecular weight of the non-aggregated form of MAIF prepared by the method described above was found to be less than 10,000 daltons. This was deduced from the fact that the first step in the isolation of MAIF from whey was by ultrafiltration using a membrane that does not allow the passage of molecular weight species >10,000 daltons.

The MAIF has a negative charge. This was determined by applying milk ultrafiltrate to a DEAE cellulose ion exchange column. The MAIF did not elute from the column with water. Changing the elution media to sodium chloride (0.9% pH) caused the elution of several peaks (FIG. 1). Neutral and positive charged species do not adhere to the ion exchange resin, and negative charged species are eluted by increasing the salt concentration. When the less than 10,000 dalton molecular weight permeate was applied to the DEAE column, neutral salts and sugars eluted with water (Peak 1, FIG. 1). Three distinct peaks eluted when the buffer was changed to saline (Peaks 2-4). The second peak and its shoulder contained MAIF biological activity in the rat assay. It is concluded, therefore, that the MAIF has a negative charge.

Another chemical characteristic of the MAIF is that it forms an aggregate during the process of removing salt. This property becomes apparent when <10,000 dalton molecular weight permeate was passed over a Sephadex G-10 column, equilibrated with double distilled water and eluted with water at a pH of 7 (FIG. 2). Three peaks eluted from the G-10 column; the first peak eluted with the void volume suggesting a molecular weight equal to or greater than 10,000 dalton. This was unexpected because molecules greater than 10,000 daltons had previously been removed from this sample by ultrafiltration. The second peak eluted in the position expected for the anti-inflammatory factor. Both the first and second peaks exhibited anti-inflammatory biological activity in the rat paw assay, whereas the third peak lacked activity. It was surprising to find that both the first and second peaks had anti-inflammatory biological activity. The material recovered from the first peak of the G-10 column (Step 3) was lyophilized and applied to a G-100 column; a single peak was eluted with the void volume, suggesting a molecular weight of 100,000 daltons or greater. The Step 3 G-10 column removes salt at the same time it separates the different molecular weight species. It is concluded, therefore, that during passage over the G-10 column and resulting removal of salt the anti-inflammatory factor formed a large molecular weight aggregate. The degree of aggregation varied with the salt concentration.

The aggregation property suggests the possibility that a wide spectrum of different molecular weight species can be formed which have anti-inflammatory biological activity due to the presence of the anti-inflammatory factor. The discovery of this property suggests the possibility of producing milk anti-inflammatory factors having a wide spectrum of different biochemical properties depending on the degree of aggregation of the final product. For example, formulations having longer or shorter biological half lives might be produced by using larger or smaller molecular weight aggregates, with molecular weight distribution being controlled by the salt concentration during processing. The column chromatography method described herein results in the smallest molecular weight species that has been obtained which has biological activity (i.e., peak 2 from the Step 3 G-10 column). This observation also suggests using other methods for forming the aggregates. For example, dilution in water causes the aggregation to occur. Chemical agents that bind salts, especially calcium, can cause the formation of the aggregate. Having made this discovery, other methods for forming the aggregate and separating the MAIF will be obvious to those skilled in the art.

EXAMPLE 4

Biological Activity Assay

The anti-inflammatory action of the MAIF was tested on edema that was caused by the injection of a solution of carrageenan into the footpads of rats. A lyophilized sample of the MAIF was dissolved in the appropriate vehicle and given intraperitoneally to experimental rats. The carrageenan was then administered to the rats in an amount of 0.1 ml of a 1% saline solution in each hind footpad. The footpads were measured before injections were given and 2.5 hours after the injections, using a thickness gauge. The results are illustrated in Tables 2 and 3.

The non-aggregated form of MAIF (peak 2 from the G-10 column) from control and hyperimmune milk caused reduction in inflammation of the rat paw at doses between 1 mg and 0.25 mg (Table 2). Both the hyperimmune milk and the regular milk exhibited activity; however, the hyperimmune material was more potent. We concluded from this that the MAIF occurs in greater concentration in the milk from hyperimmune cows.

The second peak from the DEAE column exhibited activity when isolated from either hyperimmune milk or regular milk. The activity is substantially greater in the hyperimmune milk (Table 3).

The first peak from the G-10 column, which is the aggregated form of MAIF, exhibited activity in rat paw tests (Table 2). However, the aggregated is not as potent as the nonaggregated form on equal water basis.

It is concluded from these studies that the MAIF factor occurs naturally in cows milk. Hyperimmunization of the cows causes higher concentration of MAIF in the milk. The MAIF is a small, negatively charged molecule that can be separated from the milk by a variety of methods. The MAIF factor can form large molecular weight aggregates that do not naturally occur in milk, but form during processing.

TABLE 2

EFFECT OF MILK ANTI-INFLAMMATORY FACTOR (MAIF) ON REDUCTION OF INFLAMMATION IN RATS

| MAIF DOSAGE | Foot Pad Measurements (mm) | | | % Inflammation |
|---|---|---|---|---|
| | Before Injection | 2.5 hr. After Injection | Difference | |
| Prepared from Hyperimmune Milk | | | | |
| 2.0 mg/rat | 3.43 | 5.01 | 1.58 | 46 |
| 1.0 mg/rat | 3.49 | 5.39 | 1.90 | 54 |
| 0.5 mg/rat | 3.42 | 5.51 | 2.09 | 61 |
| 0.1 mg/rat | 3.43 | 5.86 | 2.43 | 71 |
| Control/Saline | 3.43 | 5.82 | 2.39 | 70 |
| Prepared from Normal Cows Milk | | | | |
| 2.0 mg/rat | 3.30 | 5.24 | 1.94 | 59 |
| 1.0 mg/rat | 3.31 | 5.22 | 1.91 | 58 |
| 0.5 mg/rat | 3.32 | 5.33 | 2.01 | 61 |
| 0.25 mg/rat | 3.31 | 5.42 | 2.11 | 64 |

TABLE 3

COMPARISON OF SEMIPURIFIED FRACTIONS OF MAIF ON REDUCTION OF INFLAMMATION IN RATS (Prepared From Hyperimmune and Regular Milk)

| | Foot Pad Measurements (mm) | | | |
|---|---|---|---|---|
| | Before Injection | 2.5 hr. After Injection | Difference | % Inflammation |
| DEAE Column Second Peak Hyperimmune Milk 2 mg/rat | 3.25 | 5.04 | 1.79 | 55 |
| DEAE Column Second Peak Regular Milk 2 mg/rat | 3.30 | 5.24 | 1.94 | 59 |
| G-10 Column First Peak 2 mg/rat | 3.31 | 4.98 | 1.67 | 50 |
| Control/Saline | 3.34 | 5.63 | 2.29 | 69 |

EXAMPLE 5

Chemical Analysis of Anti-inflammatory Factor

Anti-inflammatory factor samples were analyzed chemically. MAIF is not crystalline in structure, as determined by X-ray diffraction studies. MAIF preparations gave elemental analysis consistent with carbohydrate composition. The C, H, O ratios were consistent with a polymeric or oligomeric material with some carbinol groups being oxidized to carboxyl. The slight excess of calcium equivalents over chloride ions may be accounted for in part as carboxylate salts. The remainder may be sodium or potassium salts. However, the melting behavior, or rather the nonmelting behavior, was suggestive of salt-like and/or higher molecular weight compositions. The material in the present state of purity apparently contains a variable amount of salts of calcium and chloride, probably $CaCl_2$.

Neither preparation contained a significant amount of nitrogen which precludes any peptide component in its composition. Likewise, the absence of significant nitrogen can rule out the presence of amino sugars and other nitrogencontaining materials such as various complex lipids as the major component(s).

Pyrolytic mass spectra revealed significant traces of 18-carbon fatty acids. This fact, taken together with traces of N and P, suggest the presence of a complex lipid in the factor.

Infrared spectroscopy revealed absorptions consistent with carbinol and carboxylate functionalities. Ultraviolet, visible and fluorescent spectroscopy revealed no significant amount of chromophores beyond those indicated by infrared.

The chemical tests are consistent with an oligomeric carbohydrate, wherein the carbonyl function (aldehyde or ketone) is tied up in the subunit linkages. The oligomeric carbohydrate also contains such side-chain oxidation to carboxylate.

The MAIF preparation is substantially, but not completely pure.

EXAMPLE 6

Rat Paw Edema Tests: Oral Administration

Figure 3:
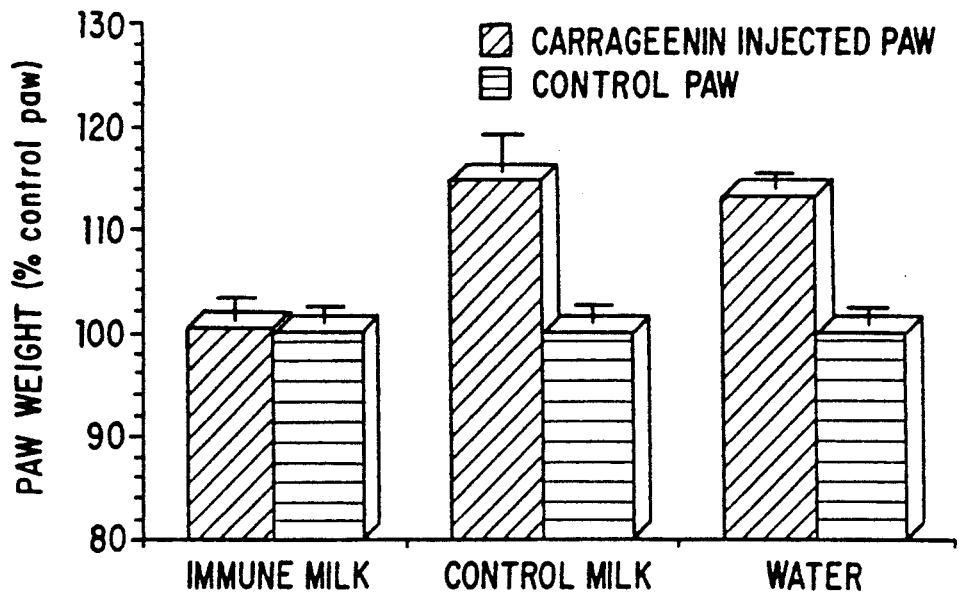
FIG. 3. Effect of immune milk on carrageenan-induced edema in rats (paw weight, % control paw, mean ±sem, n=10).

The rat carrageenan footpad assay was used to test the effectiveness of MAIF as an in vivo anti-inflammatory agent. Thirty adult white rats were randomly divided into three groups of ten rats per group. The groups received, in five consecutive daily treatments, either 10 mg of skim milk powder from hyperimmunized animals, 10 mg of skim milk powder from nonimmunized animals or not treatment (20 ml water per day only). The powders were orally administered in 20 ml of water. On the fifth day the right paw of each rat was injected with 0.1 ml of 1% carrageenan in saline. This procedure is known to cause acute inflammation (edema). Twenty-four hours after injection, the rats were sacrificed, the paws amputated, and the weights of the left (control) and right (edematous) paws were compared. The results of the assay as shown in Table 4 (expressed as weight in grams) and in FIG. 3 (expressed as a percentage of the average weight of control paws).

TABLE 4

Rat Paw Edema Test Results
(Paw wt, g, mean ± sem, n = 10)

| Treatment | Carrageenan Paw (wt, g) | Control Paw (wt, g) | Difference (g) |
|---|---|---|---|
| Immune Milk | 1.78 + 0.03 | 1.71 + 0.02 | 0.06 + 0.02 |
| Control Milk | 1.88 + 0.06 | 1.64 + 0.03 | 0.24 + 0.05 |
| Water | 1.86 + 0.03 | 1.65 + 0.03 | 0.22 + 0.02 |

The inflammatory response to carrageenan injection was markedly reduced in the immune milk treated rats as compared with the nonimmune milk and water control groups. No evidence of side effects or adverse effects on the general health of the rats was detected. From these data it can be concluded that daily consumption of skim milk powder from hyperimmunized animals almost completely blocked the inflammatory response induced by carrageenan injection in the footpad of rats.

EXAMPLE 7

Quantitative Rat Paw Edema Tests

A series of experiments was conducted on the hyperimmune milk fraction. The experiments were designed to confirm the anti-inflammatory activity of MAIF when given intraperitoneally and to establish a dose response curve, explore alternative routes of administration, and investigate dosage regimens which might form the basis of further investigations.

Peak I from the G-10 column, supplied by Stolle Milk Biologics International, was prepared according to the methods described in U.S. Pat. No. 4,956,349. Lactose, obtained from commercial sources, was used as a placebo. Aspirin was used as a positive control. Aspirin was dissolved in water and given orally by gastric gavage at the ratio of 200 mg per kilogram, a dose known to be active in the assay. A 2% solution of kappa carrageenan (Sigma C-1263) has been found to produce the most reproducible results and was thus used in these experiments. The footpad assay was modified by using isotopically labeled human serum albumin ($^{125}$I-HSA) that localizes in the carrageenan-induced lesion in direct proportion to the volume of the exudate. By determining the total radioactive count in the footpad and comparing this to the counts in a known volume of plasma from the injected animal, a direct measurement of edema in microliters of plasma equivalents is obtained. $^{125}$I-HSA was injected intravenously at a dose of 1.0 microcurie per rat. Female Dark Agouti rats were used. The rats were approximately 12 weeks old, weighed between 160 grams and 200 grams, and were obtained from the in-house inbred colony.

To conduct the carrageenan footpad assay, 0.1 ml of 2% carrageenan was injected subcutaneously into each hind foot pad of an anesthetized rat. This injection was followed immediately by injection of 1.0 microcurie of $^{125}$I-HSA in 0.5 ml of saline into the tail vein. After four hours, each rat was weighed, blood samples obtained, and the rat euthanized. Both hind feet were then removed and the levels of radioactivity in each foot and in the 200 μl plasma standard were measured in an automated gamma counter. From these measurements the volume of edema in each foot was calculated and expressed in microliters.

Experiment 1: Intraperitoneal Dose Response

Figure 4:
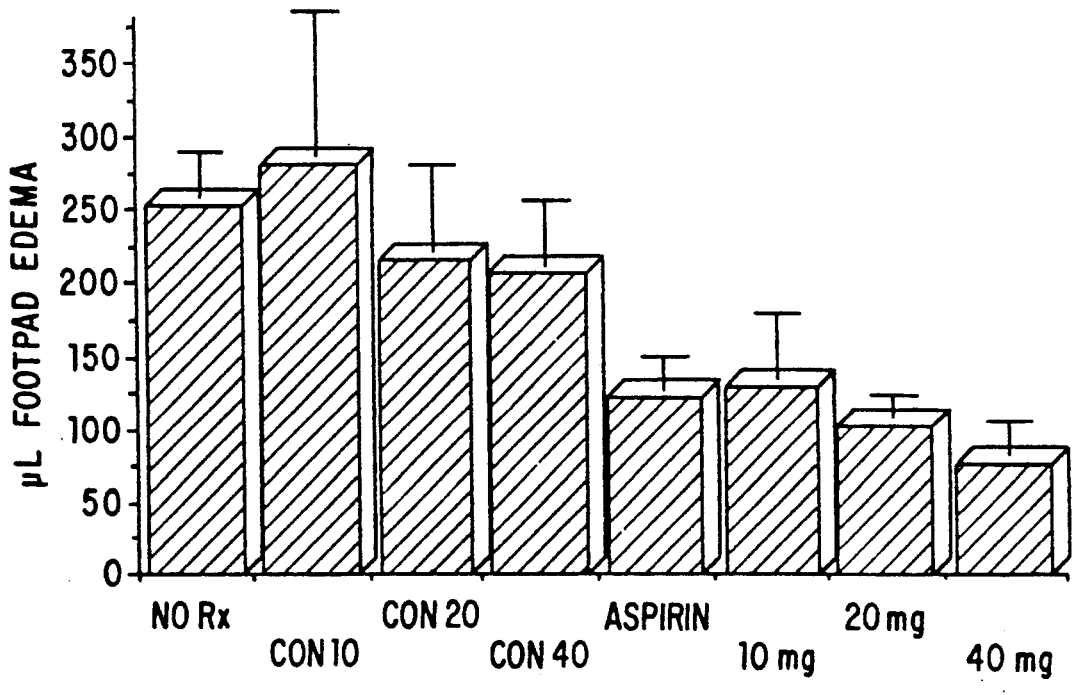
FIG. 4. Effect of intraperitoneal MAIF on footpad edema in rats (μL, means ±SC, n=6).

FIG. 4 illustrates the effect of intraperitoneal administration of MAIF compared to lactose (CON), aspirin, and no treatment (No $R_x$). All treatments (lactose, aspirin, MAIF) were given 30 minutes prior to the injection of carrageenan.

Figure 5:
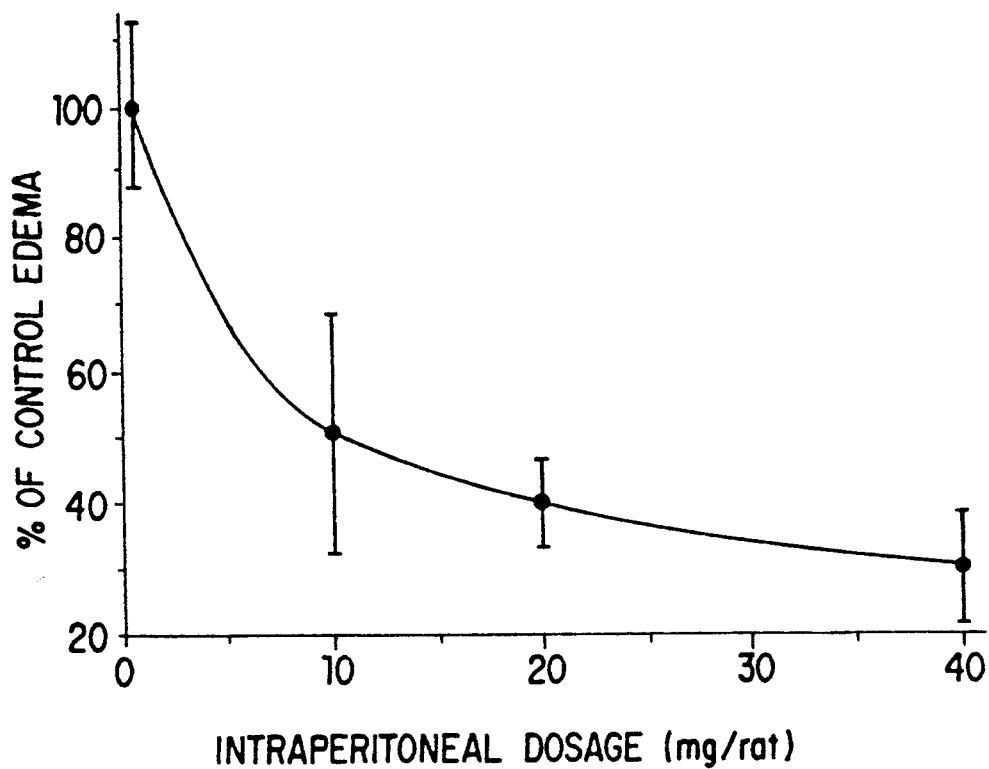
FIG. 5. Intraperitoneal dose-response curve for MAIF in rat paw edema test (% control, means±SD, n=6).

Carrageenan injection resulted in edema averaging 250 μl (No $R_x$). The edema was inhibited by aspirin and all dosages of MAIF but was not inhibited by lactose. The intraperitoneal MAIF dose-response curve, derived by expressing the data as percentage of average control (no treatment) edema is shown in FIG. 5.

Experiment 2: Effects of Various Routes of MAIF Administration

Figure 6:
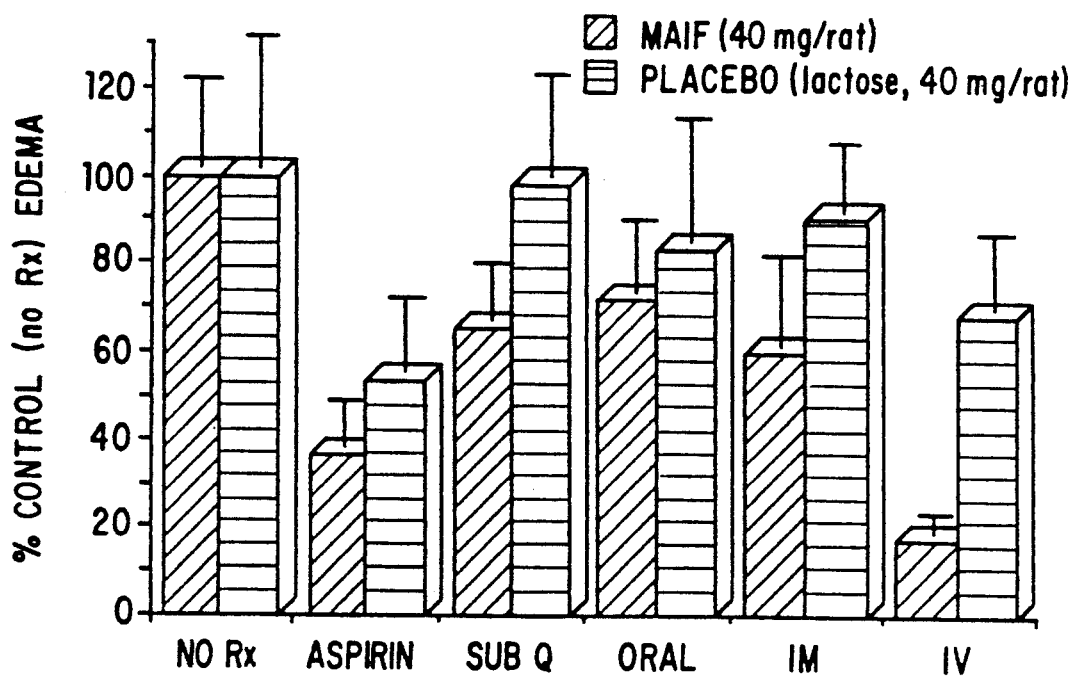
FIG. 6. Effect of hyperimmune milk factor (MAIF) vs. placebo (lactose) on footpad edema in rats (% control), means ±SD, n=6).

FIG. 6 illustrates the effect, on footpad edema, of the administration of lactose and MAIF orally (ORAL), intramuscularly (IM), subcutaneously (SUB Q), and intraveneously (IV). Also shown are a positive control (aspirin) and a nontreated control (NO $R_x$).

The preparations were administered prior to carageenan challenge according to the following schedule: Aspirin: orally, 30 minutes prior; Subcutaneous MAIF: 1 hour prior; Oral MAIF: 24, 16 and 1 hour prior; intramuscular MAIF: 30 minutes prior; intravenous MAIF: at the time of challenge (isotope was also injected).

The results indicate that, expressed as the percentage of average control edema in each separate assay, MAIF, by all routes of administration, inhibited edema formation. Forty milligrams of MAIF given intraveneously almost completely abrogated the inflammatory response to carrageenan. These results demonstrate the anti-inflammatory activity of MAIF and, in view of the results of Experiment 1 above, suggest that the order of effectiveness for different routes of MAIF is IV>IP->IM>SUB Q>ORAL.

Figure 7:
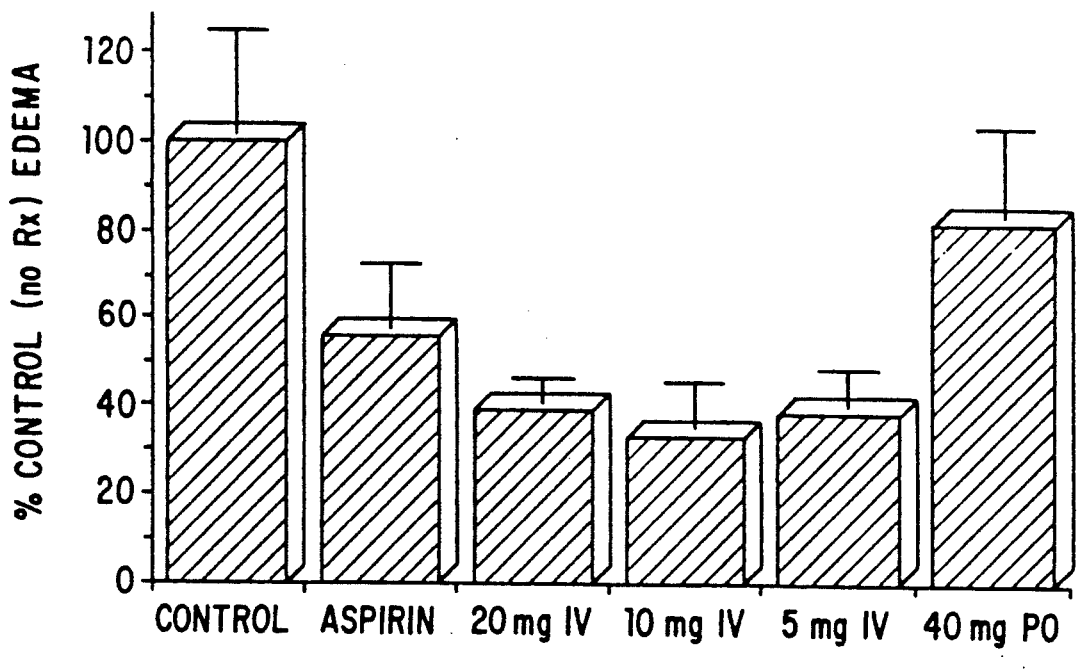
FIG. 7. Effect of iv and oral MAIF on footpad edema in rats (% control, mean ±SD, n=6).

Experiment 3: Effect on Edema of Intravenous and Extended Oral Administration: Dose Response FIG. 7 shows the effects of IV and oral MAIF administration on footpad edema in rats. MAIF oral treatment (40 mg per rat per day) was given daily for six days and also one hour before carrageenan challenge (PO). Intravenous treatments (5, 10, 20 mg) were given at the time of carrageenan challenge (IV). Also shown are a positive control (aspirin) and a negative control (no treatment).

The results shown in FIG. 7 indicate that all three MAIF dosages result in anti-inflammatory activity that exceeds even the activity of aspirin in the assay, whereas extended oral administration results in marked but limited activity.

Figure 8:
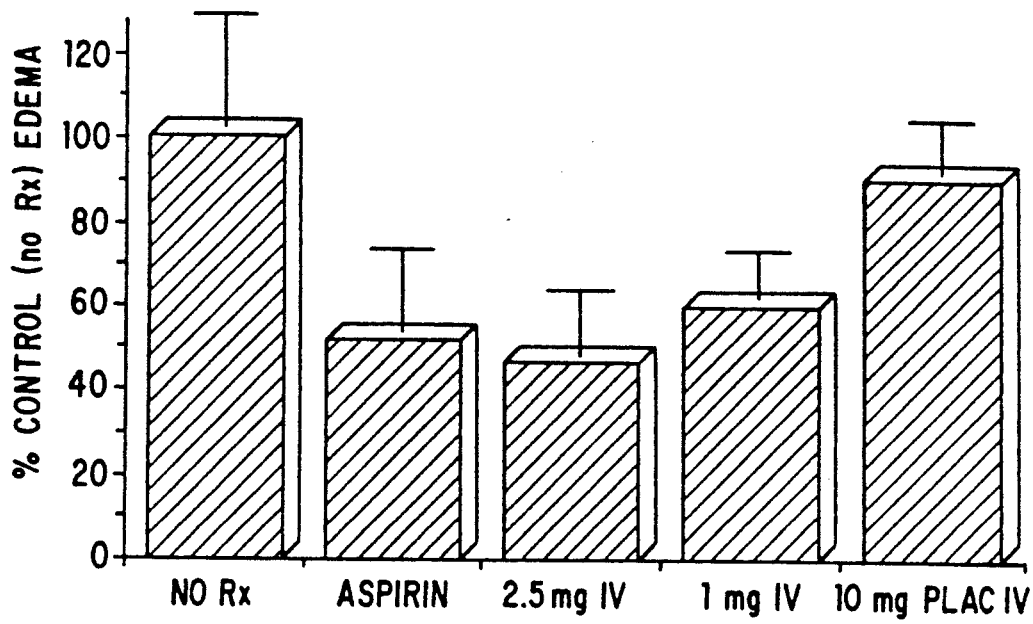
FIG. 8. Effect of low iv dosage of MAIF on footpad edema in rats (% control, mean±SD, n=6).

The study was therefore extended to examine the effects of further reduced intravenous dosages of MAIF. Intravenous dosages of lactose placebo were included as a control. The results of these studies are shown in FIG. 8. Intravenous dosages of 2.5 and 1 mg MAIF (IV) induced anti-inflammatory activity in the range of the activity induced by aspirin. 10 ml of intravenous lactose placebo (10 mg PLAC IV) did not induce activity in that range.

Figure 9:
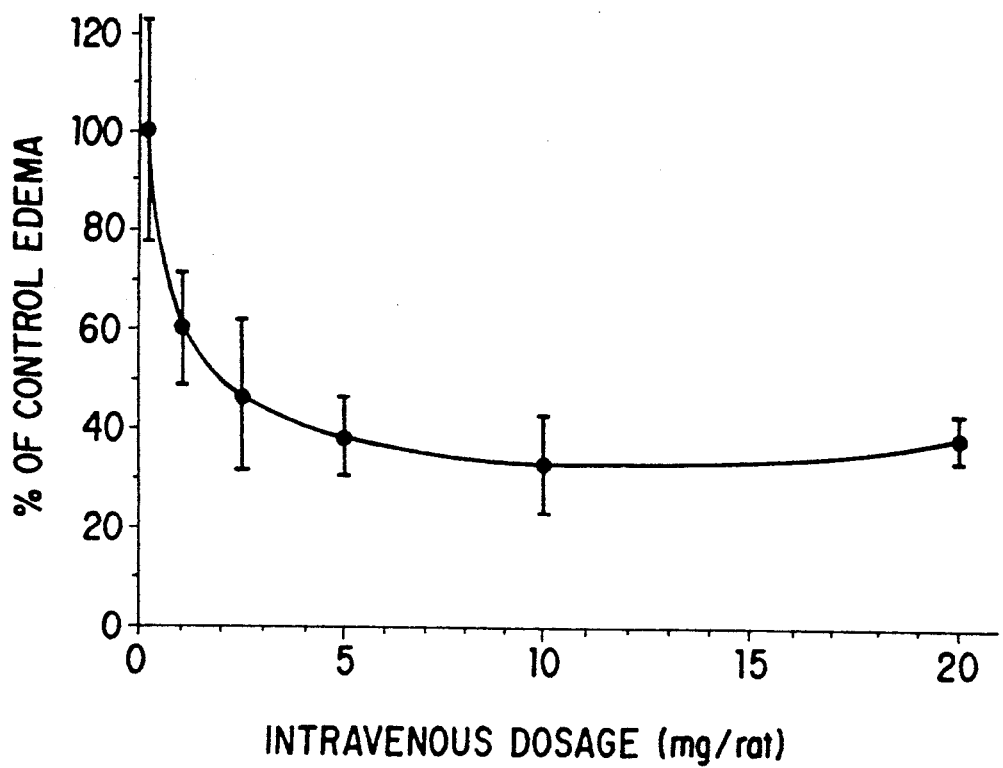
FIG. 9. Intravenous dose-response curve for MAIF in rat paw edema test (% control, mean±SD, n=6).

An intravenous dose response curve was derived by combining the results of Experiments 2 and 3 and expressing these results as percentage average control edema (no treatment) in each separate assay. The curse is shown in FIG. 9.

The conclusions that may be drawn from the quantitative rat paw edema tests are as follows: milk fraction peak I from the G-10 column, extracted and purified as described in U.S. Pat. No. 4,956,349, consistently shows anti-inflammatory activity when tested in the rat paw edema model. A dosage of 4 mgs MAIF per rat given intravenously at the time of carrageenan injection is sufficient to drastically inhibit edema and was therefore chosen as a standard against which other preparations would be compared in further experiments.

EXAMPLE 8

Anti-Inflammatory Properties of Preparations of Hyperimmune Milk Obtained from Identical Twin Cows The effect of vaccination on the anti-inflammatory activity of milk was investigated by testing the bioactivity of various milk fractions obtained from identical twin cows. Based on the extraction methods described in U.S. Pat. No. 4,956,349, an extraction scheme utilizing ultra-filtration was devised. The processing sequence was as follows:

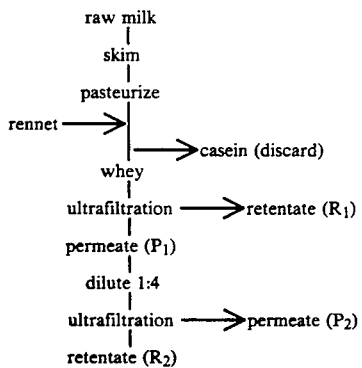

Milk samples were prepared from immunized twin cows, non-immunized control twin cows, and reconstituted skim milk powder previously prepared from immunized cows. The sample group consisted of 45 sets of identical twin cows. One cow of each twin set was vaccinated bi-weekly with Stolle S100 mixed bacterin (described in U.S. Pat. No. 4,956,349). The bioactivity of the various fractions was tested by intravenous injection using the rat caraageenan footpad assay described above.

The hypotheses to be tested were that (a) hyperimmunization was responsible for the anti-inflammatory activity described above. (b) MAIF could be extracted on a commercial scale by ultra-filtration, and (c) dilution of the permeate would cause aggregation of the anti-inflammatory factor, causing it to be retained by the 30,000 molecular weight ultra-filtration membrane.

Figure 10:
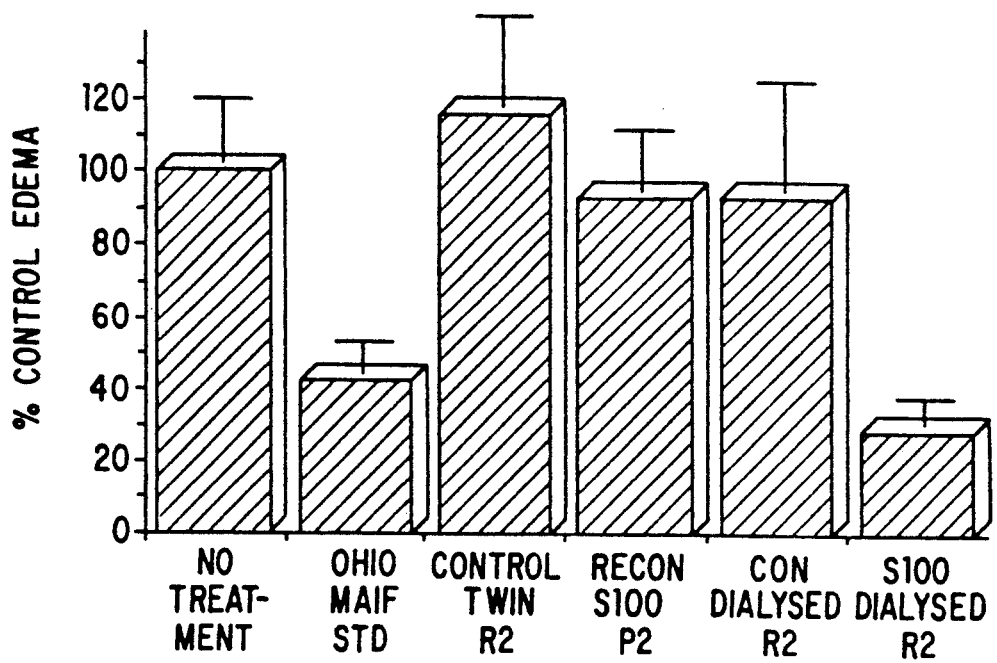
FIG. 10. Run 1, twin herd/ultrafiltration experiments (% average control edema, mean±SD, n=6).

FIG. 10 illustrates the results of a twin herd ultra-filtration experiment designed to test the bioactivity of various fractions made from the milk of non-vaccinated control twins and from reconstituted milk powder from immunized cows. The fractions that were tested are as follows: Peak I, G-10 column preparation, 4 mls (OHIO MAIF STD); $R_2$ final retentate from non-vaccinated twin (CONTROL MILK $R_2$); $P_2$ final permeate from the reconstituted milk powder (RECON S100 $P_2$); dialyzed $R_2$ final retentate from non-vaccinated twin (CON DIALYZED $R_2$); dialyzed final retentate from the reconstituted milk powder (S100 DIALYZED $R_2$).

No anti-inflammatory activity could be detected in the $R_2$ final retentate fraction prepared from non-immunized cows, even after dialysis. No anti-inflammatory activity was detected in the final permeate $P_2$ fraction prepared from the reconstituted milk powder. The reconstituted milk powder retentate $R_2$ fraction, following dialysis, exhibited anti-inflammatory activity in the range of the activity of the MAIF standard.

Figure 11:
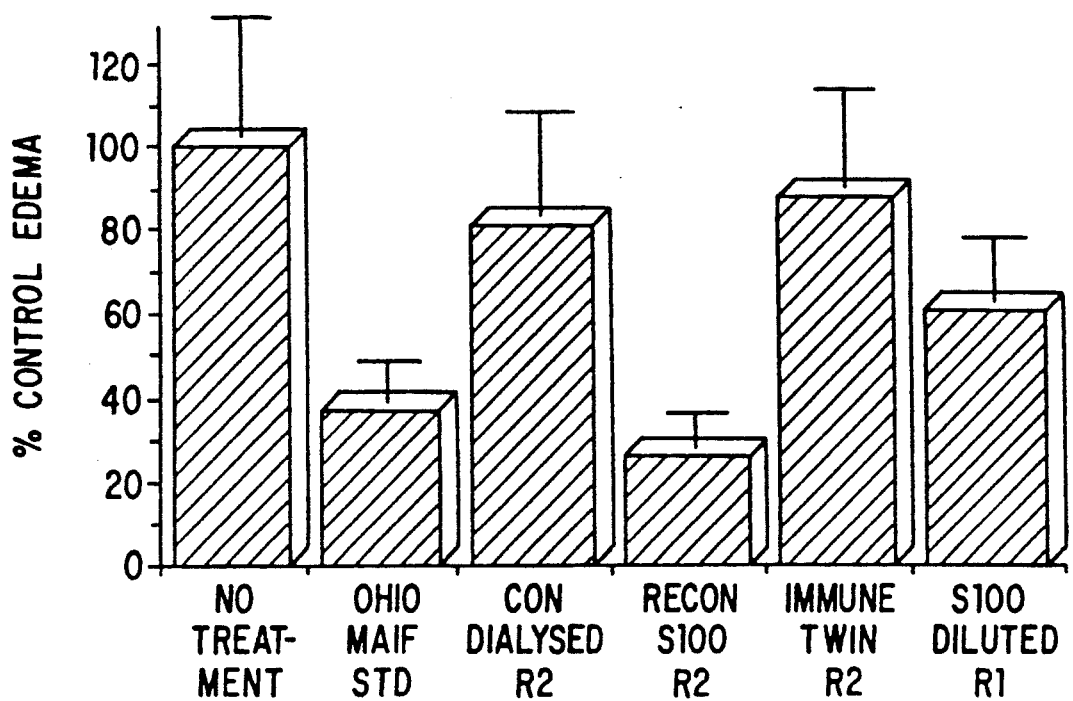
FIG. 11. Run 2, twin herd/ultrafiltration experiments (% average control edema, mean±SD, n=6).

FIG. 11 illustrates the results of twin herd ultra-filtration experiments designed to test the bioactivity of various milk fractions made from vaccinated and nonvaccinated twin cows and from reconstituted milk powder from immunized cows. The fractions that were tested are as follows: Peak I, G-10 column preparation, 4 ml (OHIO MAIF STD); dialyzed final retentate $R_2$ from non-vaccinated twins (CON DIALYZED $R_2$); final retentate $R_2$ from the reconstituted milk powder (RECON S100 $R_2$); the final retentate $R_2$ from vaccinated twins (IMMUNE TWIN $R_2$); first retentate R1 from the reconstituted milk powder, diluted for: 1 (S100 DILUTED R1).

Little anti-inflammatory activity was detected in the dialyzed retentate $R_2$ from non-vaccinated control twins or in the non-dialyzed retentate $R_2$ from the vaccinated twins. Some activity is detectable by scattergram. $R_2$ retentate prepared without dialysis from reconstituted Stolle milk powder from immunized cows was strongly anti-inflammatory. However, the preparation made by dilution of the reconstituted milk before ultrafiltration rather than dilution of whey made from the milk was only marginally active. This result indicates that anti-inflammatory activity is more efficiently extracted from the whey fraction.

Figure 12:
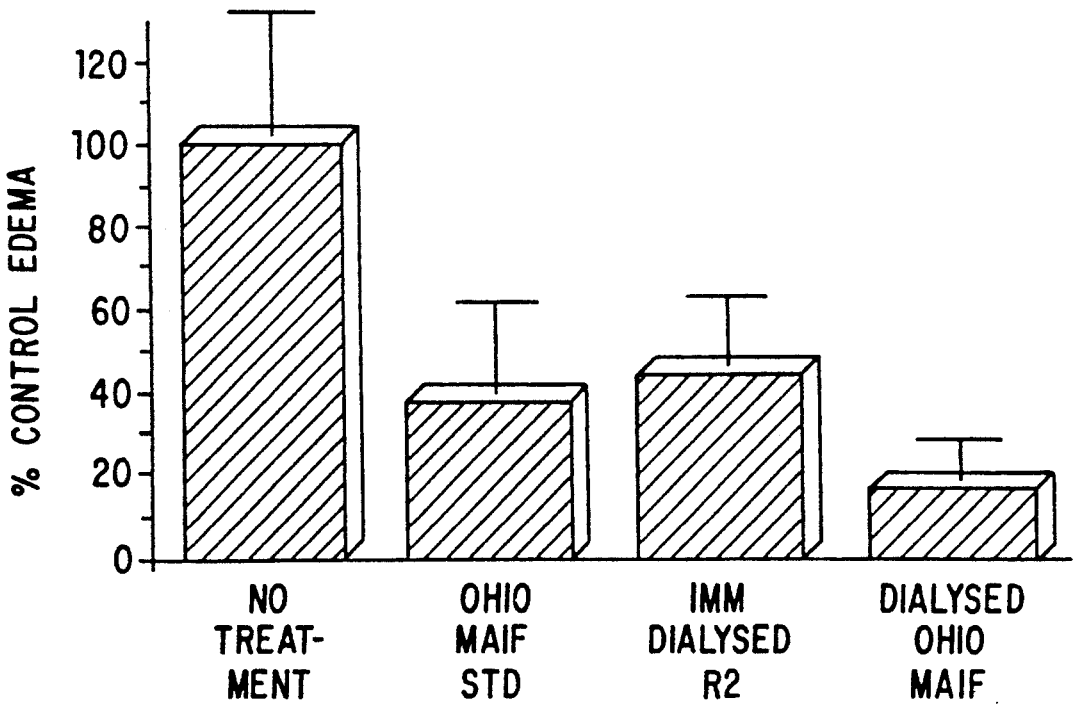
FIG. 12. Run 3, twin herd/ultrafiltration experiments (% average control edema, mean±SD, n=6).

FIG. 12 illustrates the results of twin herd ultrafiltration experiments designed to test the bioactivity of dialyzed retentate from vaccinated twin cows. The fractions tested are as follows: Peak I, G-10 column preparation (OHIO MAIF STD); dialyzed final retentate $R_2$ from vaccinated twins (IMM DIALYZED $R_2$); dialyzed final retentate from the G-10 preparation (DIALYZED OHIO MAIF). The results show that anti-inflammatory activity was present in the $R_2$ fraction from the immunized twin after dialysis. Dialyzed MAIF was more active in the assay than the nondialyzed MAIF standard. This result suggests that dialysis is an effective means of further concentrating the milk factor responsible for anti-inflammatory activity.

The results presented in FIGS. 10–12 above support the following conclusions: (1) anti-inflammatory activity can be extracted from reconstituted milk from immunized cows by ultrafiltration of the diluted permeate. (2) anti-inflammatory activity was not demonstrated in the abovepreparations that were made from the milk of non-immunized cows. (3) anti-inflammatory activity was demonstrated in the final retentate $R_2$ after ultrafiltration of diluted permeate prepared from the milk of immunized cows, but dialysis was necessary in order to demonstrate the activity.

EXAMPLE 9

Stability of MAIF, Heating, and Proteinase Treatment of MAIF

The previous evidence that the milk anti-inflammatory factor was chemically not a protein or a peptide was based largely on chemical analysis that consistently showed an almost complete absence of nitrogen. For further characterization of MAIF, several preparations were tested in the rat paw edema assay, using 4 mgs of peak I, G-10 column preparation, intravenously as the standard. The following treatments of MAIF were done: proteinase (pronase) treatment for six hours; six hours no proteinase treatment control; untreated positive control; heating at 100° C. for 30 minutes.

Figure 13:
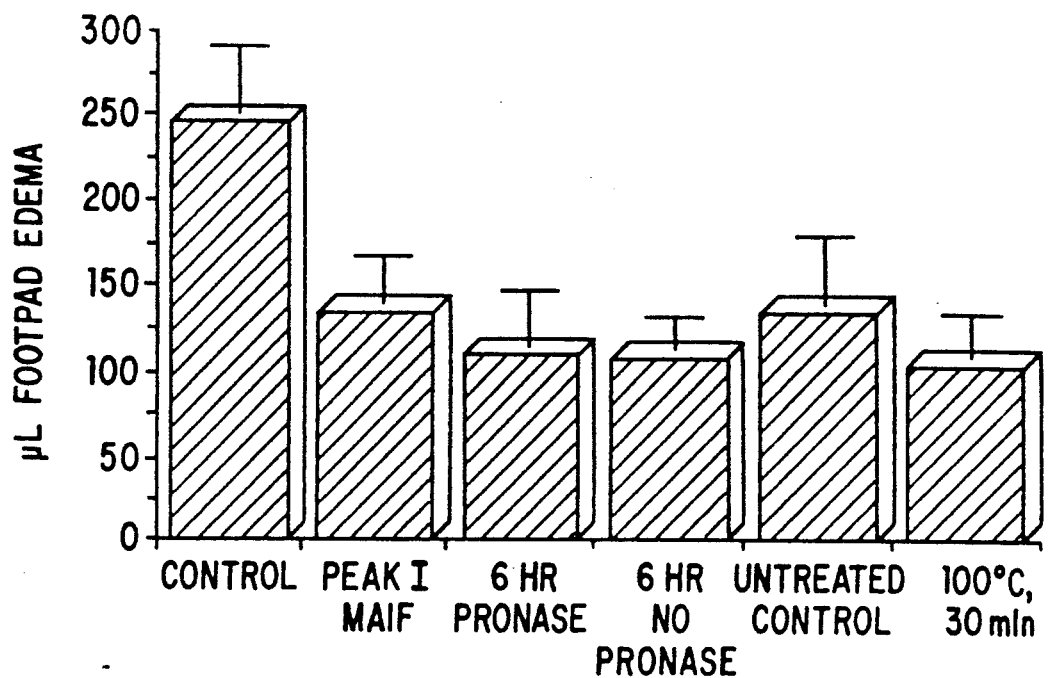
FIG. 13. Effect of various treatments of MAIF on inhibition of footpad edema in rats (μL footpad edema, mean±SD, n=6).

The results of this assay are illustrated in FIG. 13. The conclusions derived from this study were that the anti-inflammatory activity is not due to a protein or peptide and that MAIF is not inactivated by boiling. The effectiveness of pronase treatment was verified by the finding that parallel pronase treatment completely denatured milk protein.

EXAMPLE 10

Anti-Inflammatory Activity of Further Purified MAIF and Whey Protein Concentrate from Immunized Cows Retentate and permeate from ultrafiltration using an Amicon YM5 membrane were tested for biologicial activity using intravenous administration in the rat paw edema assay. In this process, the MAIF of peak I of the G-10 column, prepared according to U.S. Pat. No. 4,956,349, was further purified by ultrafiltration on an Amicon YM5 membrane. This membrane retains molecules of 5000 molecular weight or greater. Whey protein concentrates (WPCs) were also prepared from milk from immunized animals and filtered through the YM5 membrane. The following samples were tested in the assay using 4 mg peak I, G-10 column preparation, intravenously as the standard: permeate from Amicon YM5 ultrafiltration; retentate from Amicon YM5 ultrafiltration; WPC from immunized cows, 30 mgs per rat; WPC from commercial production (non-immunized cows), 30 mg per rat.

Figure 14:
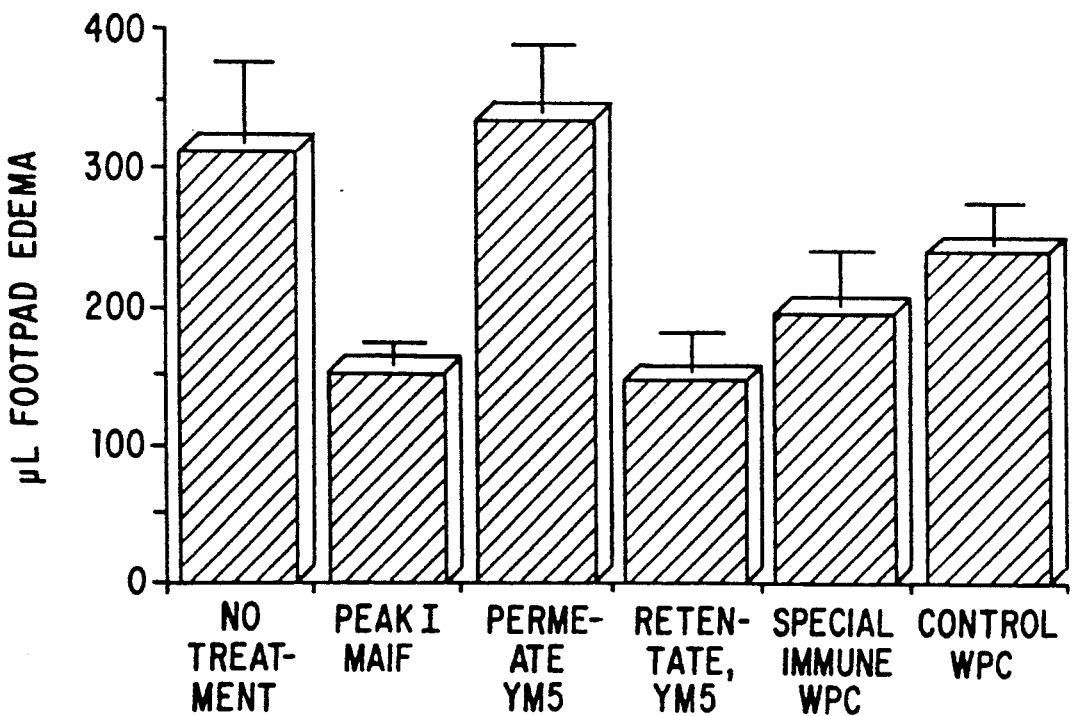
FIG. 14. Effect of fractions of MAIF and of immune wpc on inhibition of footpad edema in rats (μL footpad edema, mean ±SD, n=6).

The results of this assay are illustrated in FIG. 14. It is clear from these results that all of the activity is in the retentate which comprised approximately 0.5% of the total weight of the fraction applied to the YM5 filter. The reduction of edema seen in this experiment was achieved following administration of 20-25 micrograms of material.

Regarding the activity of WPC, WPC made from hyperimmunized animals clearly showed anti-inflammatory activity as expected. Interestingly, WPC made from non-immunized animals also showed anti-inflammatory activity. The presence of anti-inflammatory activity in the milk of nonimmunized cows is not surprising since it must be a natural substance. Its detection reflects the sensitivity of the bioassay.

EXAMPLE 11

Continuous Monitoring of Carrageenan Induced Footpad Edema

Figure 15:
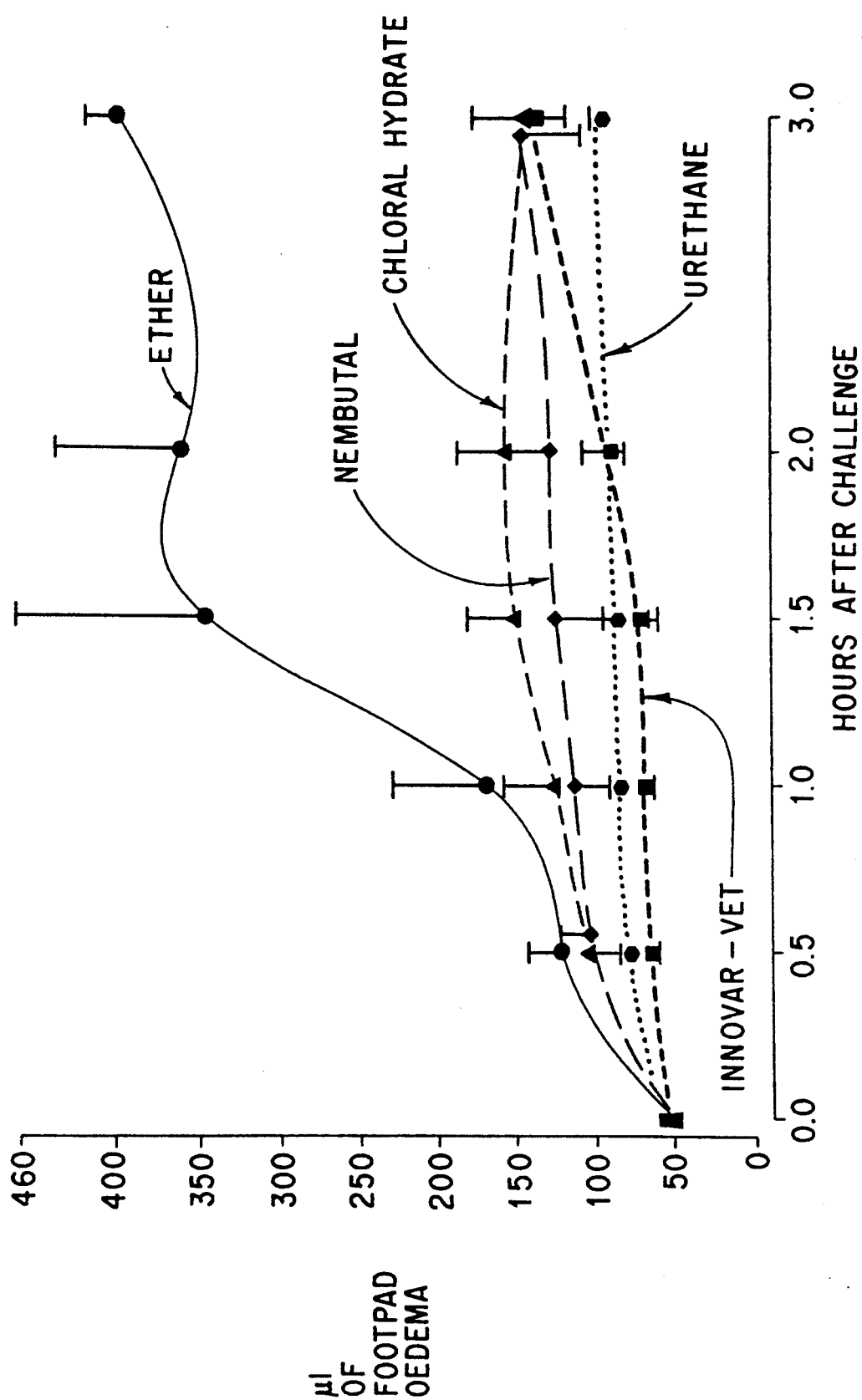
FIG. 15. Effect of five different anesthetics on the response to carrageenan in the rat footpad. The accumulation of edema was monitored at selected intervals in the same animals. n=6 for each data point.

It was established that 4 mg of MAIF given intravenously at the time of carrageenan injection reduced the accumulation of edema in the footpad by between 40% and 50%. Although these results provided evidence that the material contained an anti-inflammatory moiety, there was little indication of the site of action or pharmacological profile of MAIF. In order to obtain such data it was necessary to establish a method that allowed the continuous monitoring of footpad edema throughout the response to carrageenan. This was achieved by holding the rat foot in a demounted Gamma radiation detector. The procedure required animals to be anesthetized for up to four hours and, as anesthetics are known to suppress the inflammatory response, it was first necessary to determine the effect of anesthetics on the carrageenan-induced edema. Five agents commonly used to induce anesthesia in rats were therefore evaluated; these were ether, chloral hydrate, Innovar-vet, nembutal and urethane. The results are shown in FIG. 15.

Figure 16:
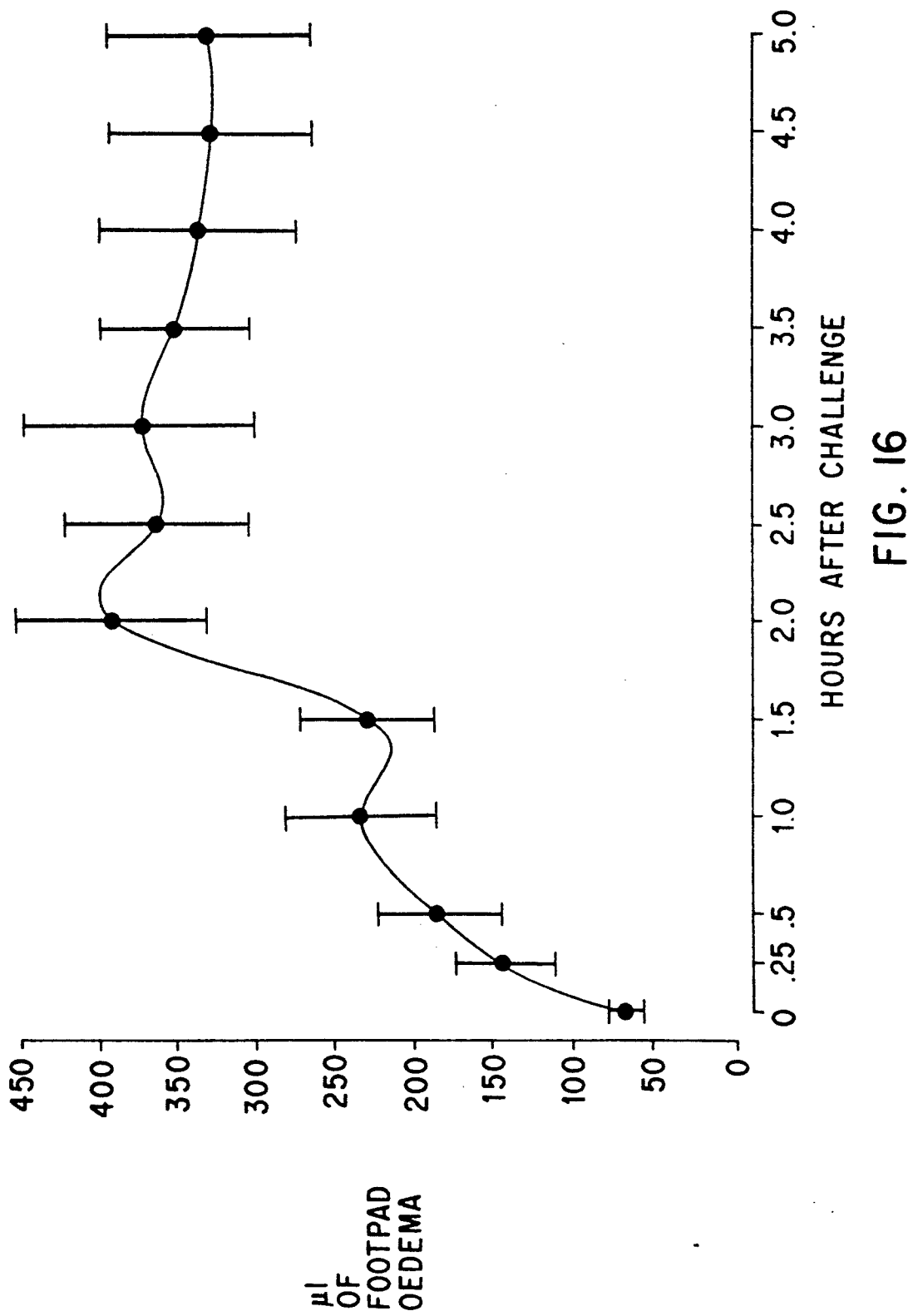
FIG. 16. Demonstration of the biphasic nature of the response to carrageenan in the rat footpad. n=5 for each data point. Ether was used as the anesthetic.

It was clear from these results that either was the anesthetic of choice when the inflammatory response was to be evaluated by this technique. The shape of the curve obtained when ether was used indicated a biphasic response. To delineate the response in more detail a further experiment was carried out in which the volume of edema was measured at 12 time points over a 5 hour period. The results confirmed a biphasic response. The early response occurred between 0 and 1 hour after challenge and late phase response between 1.5 and 2 hours (FIG. 16).

The two phases, which have also been observed by other investigators, have been termed the non-phagocytic inflammatory response (NPIR) and the phagocytic inflammatory response (PIR), respectively.

Figure 17A:
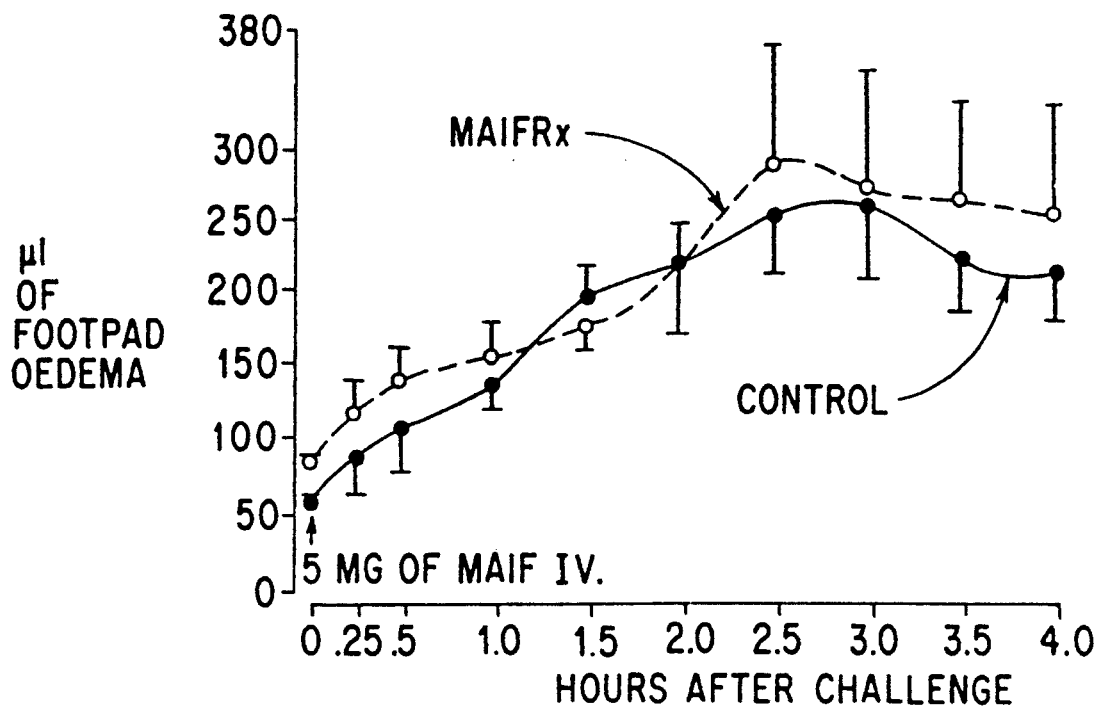
FIG. 17. MAIF, administered at either 5 mg per rat (A) or 40 mg per rat (B) does not inhibit the inflammatory response to carrageenan in ether-anesthetized rats. n=4 for all data points.
Figure 17B:
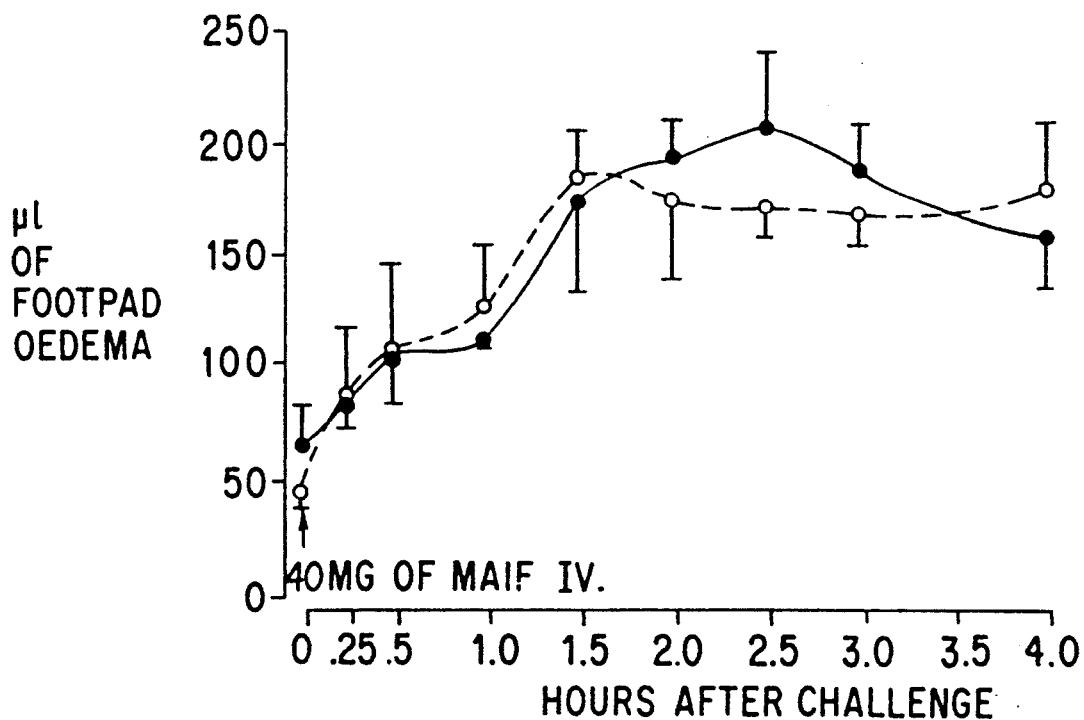

The NPIR is initiated, in response to injury, by soluble mediators such as histamine and bradykinin while the PIR depends on the participation of neutrophils. The protocol, therefore, was to administer MAIF and monitor the accumulation of edema continuously in an effort to determine whether the anti-inflammatory properties of the agent were a result of an effect on the early non-cellular (NPIR) or the later cellular (PIR) phase. 5 mg or 40 mg of MAIF/rat were administered intravenously at the time of carrageenan challenge and the accumulation of edema monitored at regular intervals over a four hour period. Neither dose affected the accumulation of edema during either phase (FIG. 17).

This result was surprising as many previous analyses, in which the effect of MAIF on carrageenan induced oedema 4 hours after challenge was determined, had demonstrated considerable anti-inflammatory activity in the fraction. It was likely, therefore, that the continuous exposure to ether suppressed or inactivated the active anti-inflammatory component of MAIF in vivo.

Figure 18:
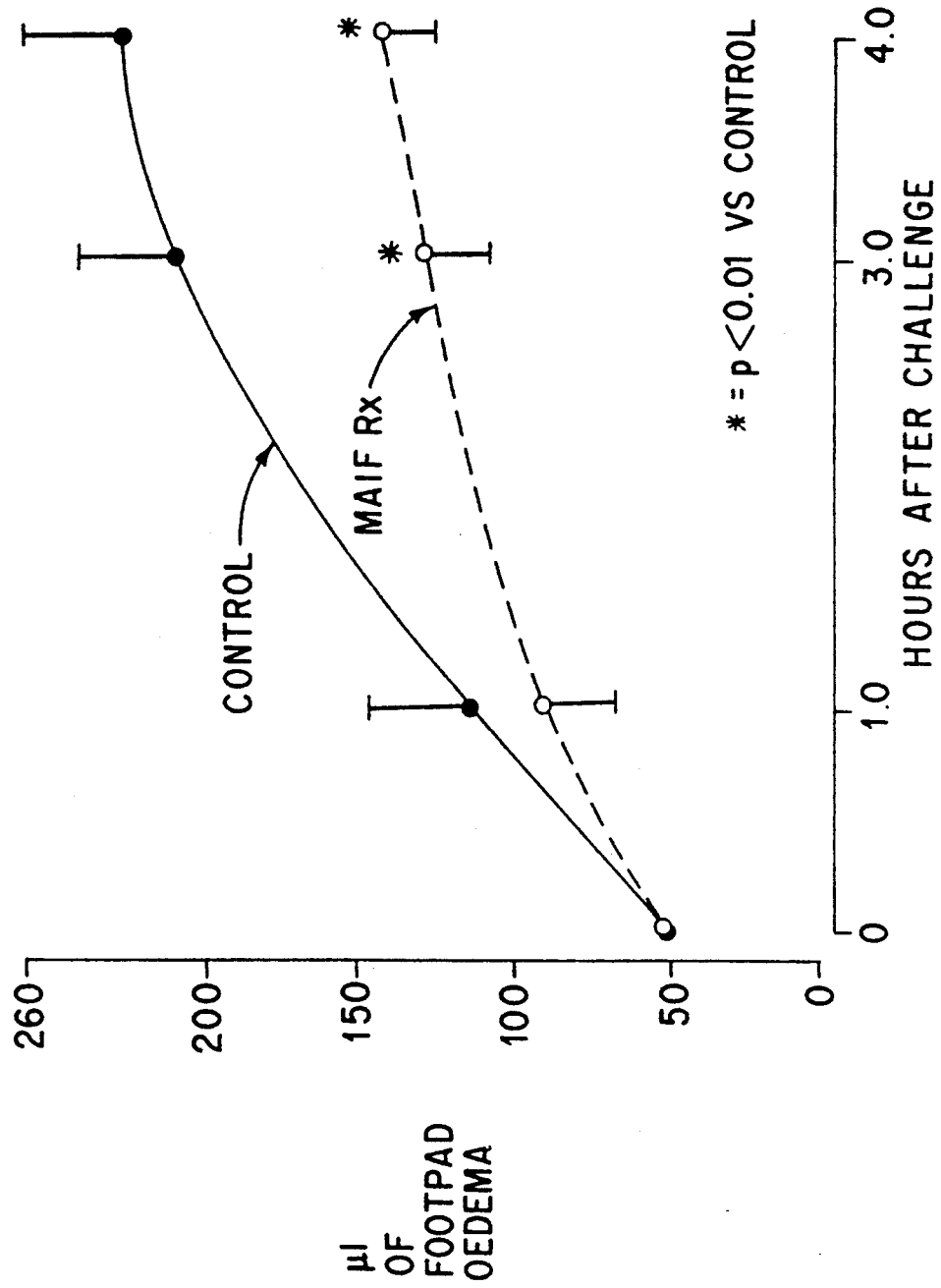
FIG. 18. Suppression of carrageenan-induced edema accumulation during the secondary, phagocytic-cell mediated, response by 40 mg of MAIF injected i.v. at the time of carrageenan challenge (time 0). n=12 for each data point in the control group and n=10 for each data point in the MAIF-treated group.

Previous studies indicated that short term exposure to ether did not affect the activity of MAIF. Therefore, an experiment was done in which the effect of MAIF on progressive edema accumulation was determined at only four time points, 0, 1, 3 and 4 hours, thus limiting the exposure of the animals to ether. The 1 hour time point was chosen to assess the affect on the early non-phagocytic inflammatory response while the 3 and 4 hour measurements were selected to quantify the effect on the later phagocytic inflammatory response. In this experiment MAIF, administered at 40 mg resulted in a reduction in the accumulation of edema during the secondary, phagocytic-cell mediated phase, but had no significant effect on the primary, soluble mediator driven phase (FIG. 18).

The following conclusions can be drawn from this series of experiments.
1. Ether is the preferred anesthetic for use in experiments where the inflammatory response to carrageenan is to be monitored continuously.
2. Continuous ether anesthesia inhibits the in vivo anti-inflammatory activity of MAIF in the carrageenan footpad assay.
3. MAIF ameliorates inflammation by inhibiting the late, phagocytic-cell mediated phase of the inflammatory response to carrageenan.

EXAMPLE 12

Time Course of the Effect of MAIF on Carrageenan Induced Footpad Edema

A further series of experiments were carried out in which the agent was administered at selected time points before or after the injection of carrageenan rather than at the time of challenge. The purpose of the study was to provide information on
(a) the most effective time for administration of MAIF in relation to the inflammatory stimulus.
(b) the biological half life of the anti-inflammatory moiety.
(c) the points in the development inflammatory response affected by MAIF.

Figure 19:
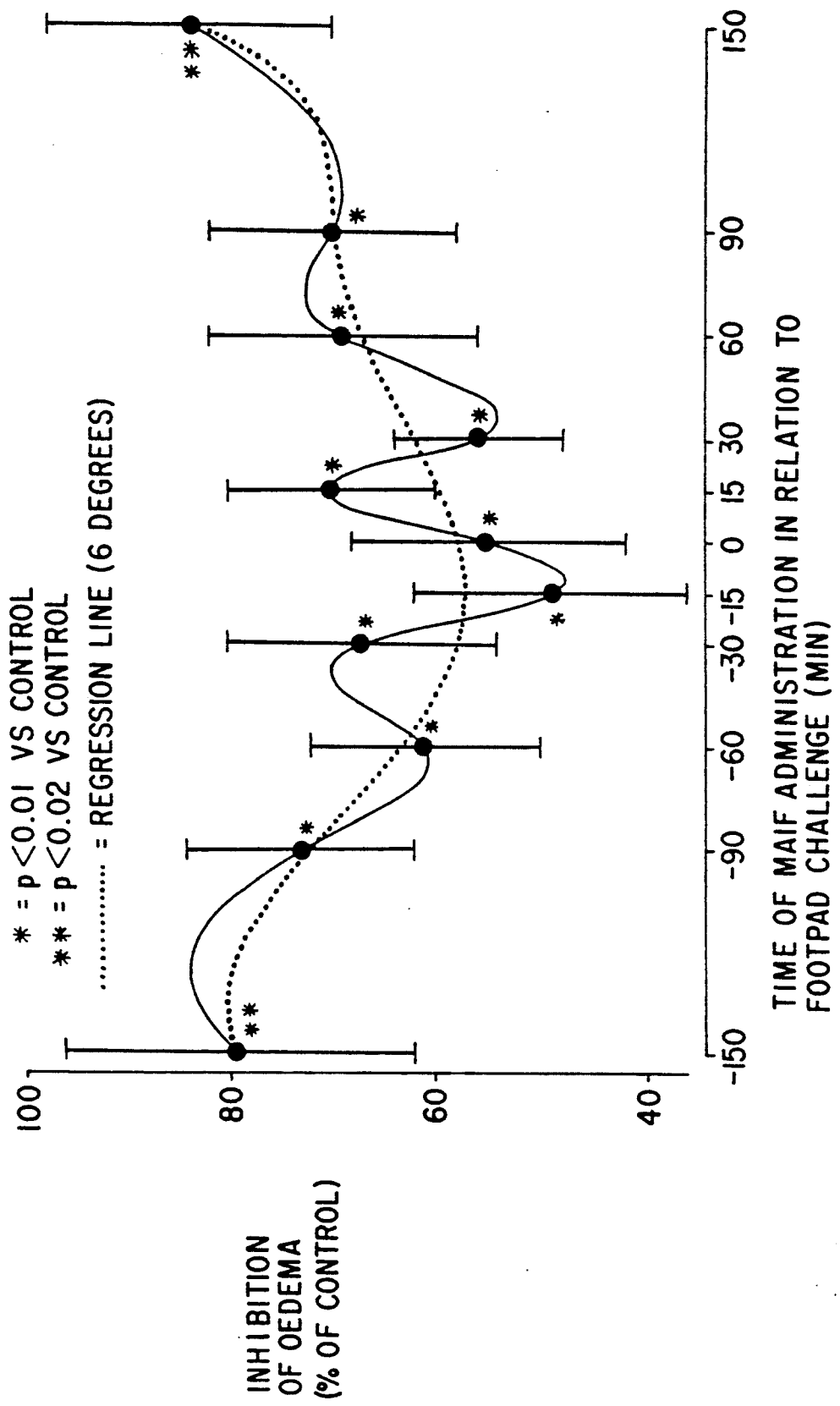
FIG. 19. Effect of MAIF, given i.v. at 4 mg per rat at different times, on the response to carrageenan in the rat footpad. Edema was assessed 4 hours after challenge in all cases. n=12 for each data point.

The study was carried out in three parts. MAIF was administered intravenously at a dose of 4 mg/rat at one of 11 time points, ranging from 150 minutes before to 150 minutes after injection of carrageenan. The results of this experiment are shown in FIG. 19 and Table 5.

TABLE 5

| Experiment | Time of A in relation to challenge (min) | Mean foot volume of control groups ($\mu l \pm$ SD) | Mean foot volume of MAIF groups ($\mu l \pm$ SD) | Inhibition of edema by MAIF (% of control volume $\pm$ SD) |
|---|---|---|---|---|
| 3 | −150 | 311 ± 65 | 246 ± 52 | 79 ± 17 |
| 2 | −90 | 304 ± 71 | 211 ± 33 | 73 ± 11 |
| 2 | −60 | 304 ± 71 | 186 ± 34 | 61 ± 11 |
| 1 | −30 | 391 ± 63 | 261 ± 49 | 67 ± 13 |
| 3 | −15 | 311 ± 65 | 152 ± 41 | 49 ± 13 |
| 1,2,3 | 0 | 336 ± 78 | 184 ± 42 | 55 ± 13 |
| 3 | 15 | 311 ± 65 | 218 ± 30 | 70 ± 10 |
| 1 | 30 | 391 ± 63 | 218 ± 30 | 56 ± 8 |
| 2 | 60 | 304 ± 71 | 212 ± 40 | 69 ± 13 |
| 2 | 90 | 304 ± 71 | 216 ± 37 | 70 ± 12 |
| 3 | 150 | 311 ± 65 | 261 ± 42 | 84 ± 14 |

A significant inhibition of edema was observed at all time points studied; however, the level of inhibition was less at the outer extremes (±150 min). An interesting cyclic response to MAIF administration was seen in those groups treated closer to the point of challenge. The fact that MAIF was more effective when given 30 minutes after challenge than when given 15 minutes after challenge supports the concept that the secondary, phagocytic-cell mediated, phase of the response is inhibited by the agent. MAIF strongly inhibited the response to carrageenan when administered 15 minutes before or at the time of challenge. It is apparent, furthermore, that the agent has a relatively long half life in the serum (1–2h) and its effectiveness is related to the time of challenge and the dynamic nature of the inflammatory response.

It is thus surmised that the anti-inflammatory effect is due to an effect on inflammatory cells, likely the neutrophils.

EXAMPLE 13

Effect of MAIF on the Reverse Passive Arthus Reaction

The possibility that MAIF might affect neutrophil involvement was investigated by evaluating the ability of the material to modulate the reverse passive Arthus reaction (RPA). This immune complex-induced response is primarily neutrophil mediated and agents which affect the development of the reaction do so via an effect on these cells. To induce the RPA, rats were injected intradermally with rabbit antibody to ovalbumin and intravenously with native ovalbumin. Ovalbumin/ovalbumin-antibody immune complexes form in and around the dermal blood vessel walls, host neutrophils bind to the Fc portion of the antibody and an intense inflammatory reaction is initiated. It should be noted that, although the response is initiated by immune-complexes, it takes place independently of the host's immune system.

Three parameters are used to quantify the RPA. These are, (1) edema—measured using the accumulation of $^{125}$I-HSA, (2) hemorrhage—assessed by invivo pre-labelling of RBC's with $^{53}$Fe and (3) neutrophil accumulation—measured by determining tissue levels of the neutrophils specific enzyme myeloperoxidase (MPO). These assays are known to those of ordinary skill in the art.

Figures 20A, 20B, 20C:
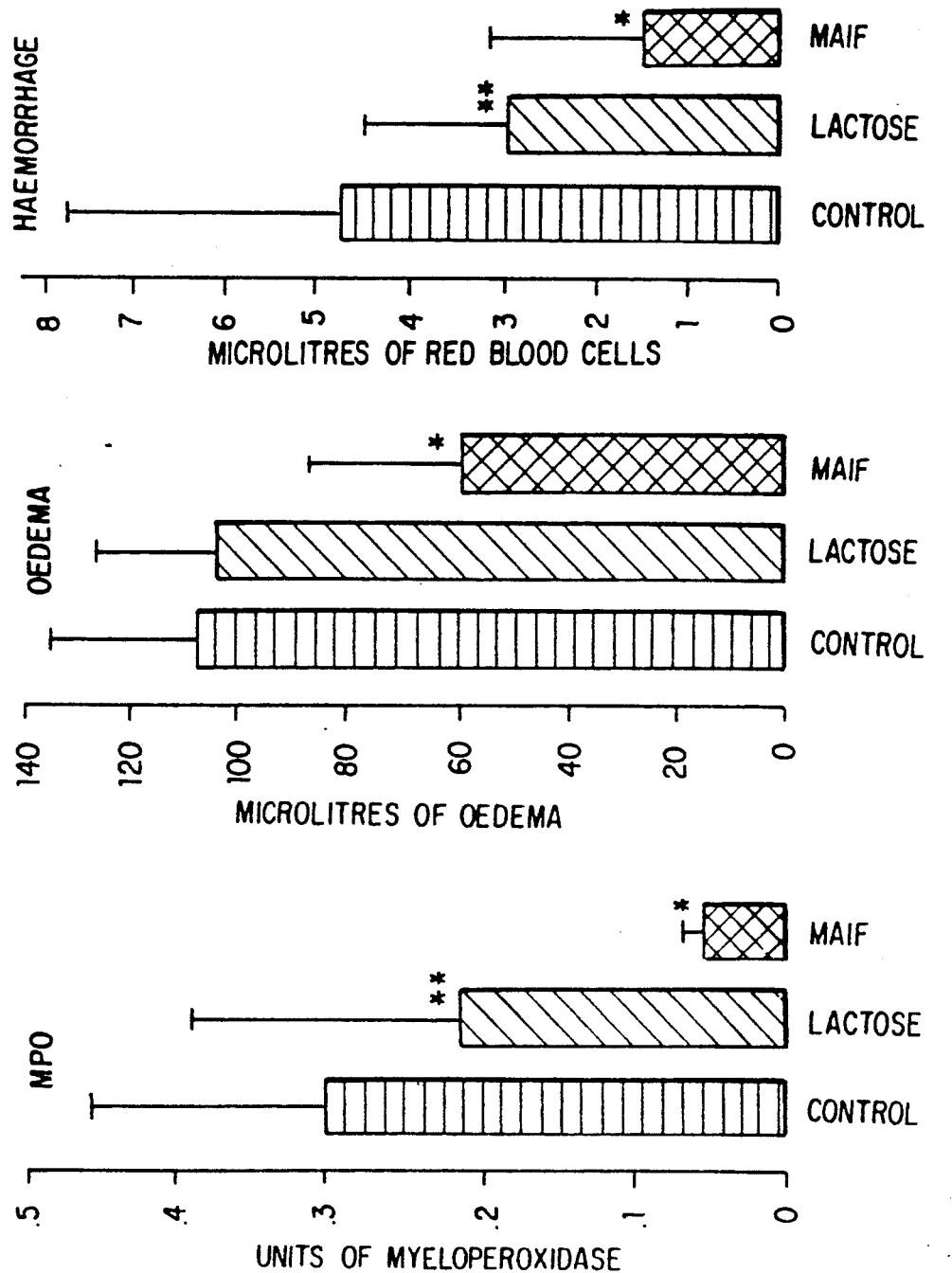
FIG. 20. Effect of 20 mg of MAIF injected i.v. on the reverse passive Arthus reaction. *=p<0.01; **=p<0.05.

Eighteen rats were divided into three groups of six. Rabbit anti-ovalbumin (40 $\mu$l) was injected intradermally at four sites on the back of each animal and 2 mg of ovalbumin injected intravenously immediately afterwards. One group of animals received no other treatment and served as controls. The second group were injected intravenously with 20 mg of a lactose preparation, while the final group were injected intravenously with 20 mg of MAIF. Both lactose and MAIF were administered with the ovalbumin. The severity of the reaction was assessed 3.5 hours after challenge. When MAIF was administered intravenously at a dose of 20 mg/rat prior to the initiation of the RPA response, there was a highly significant inhibition of the three parameters used to measure the response (Table 6, FIG. 20). The lactose control material also caused a modest and marginally significant suppression of neutrophil accumulation and hemorrhage. This indicates that there is a small amount of anti-inflammatory activity in normal milk.

TABLE 6

| Group | Neutrophil accumulation: Units of MPO | $\mu$l of Edema | Haemorrhage: $\mu$l of RBC |
|---|---|---|---|
| Control | 0.30 ± .157 | 107 ± 29 | 4.8 ± 3.1 |
| Lactose | 0.214 ± .176** | 104 ± 23 | 3.0 ± 1.5** |
| MAIF | 0.056 ± .013 | 60 ± 27* | 1.5 ± 1.7* |

* = $p < 0.01$
** = $p < 0.05$

As the neutrophil is the primary mediator of the RPA, these results provided additional evidence that MAIF was capable of inhibiting the inflammatory response via an effect on neutrophil function.

EXAMPLE 14

Effect of MAIF on Neutrophil Migration from the Vasculature

In order to participate effectively in an inflammatory response, neutrophils must first migrate from the vasculature to the site of inflammation. To determine whether MAIF interfered with neutrophil migration, a model of inflammation employing the subcutaneous implantation of sterile polyurethane sponges was used. The sponges are removed at intervals after implantation and by weighing the sponges and then extracting and counting the cells in the infiltrate, both the fluid and cellular phase of the response can be quantified. Twenty four hours after implantation >95% of the cells found in the sponge are neutrophils.

Figure 21B:
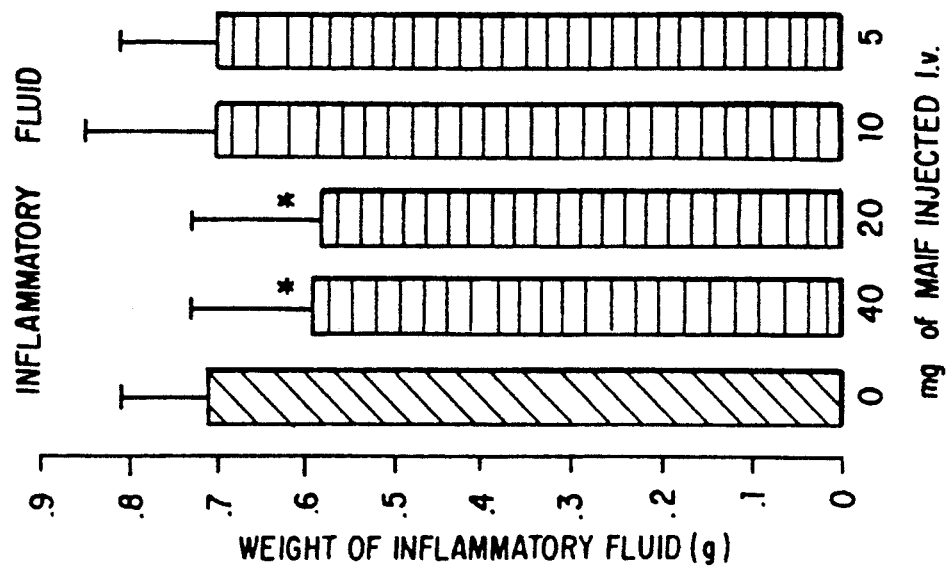
FIG. 21. Effect of decreasing doses of MAIF on the ability of neutrophils to emigrate from the vasculature into subcutaneously implanted sterile sponges. *=p<0.01.
Figure 21A:
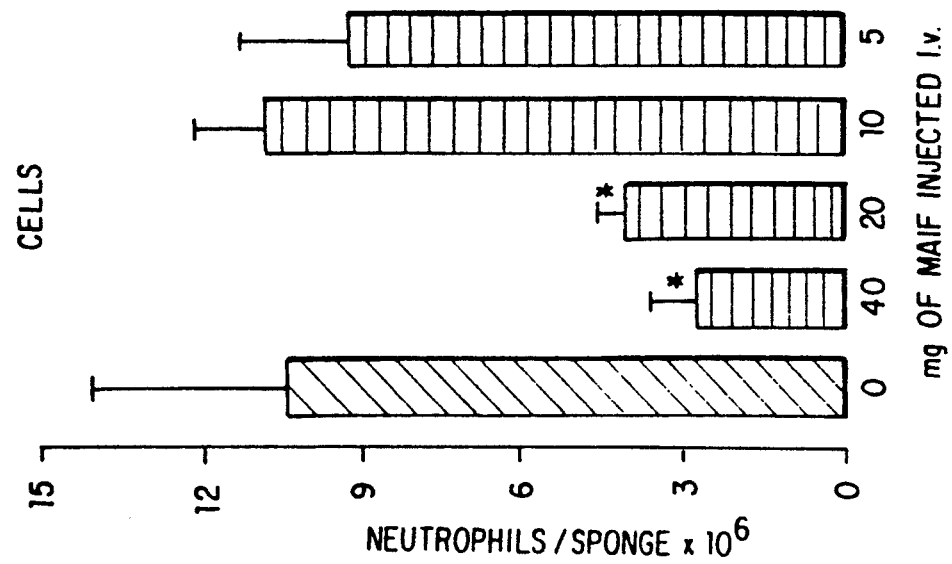

Two experiments have been carried out. In the first, animals were treated with either 5, 10, 20, or 40 mg of MAIF at the time of sponge implantation. Sponges were removed 24 hours after implantation. Each group consisted of between 5 and 8 rats and two sponges were implanted in each animal. The results are shown in FIG. 21.

Twenty or 40 mg of MAIF, administered intravenously at the time of sponge implantation, had a marked effect on the ability of inflammatory cells to migrate. A less marked, but equally significant, inhibition of fluid accumulation was also seen. The two lower doses of MAIF had no demonstrable effect in this model of inflammation.

A second experiment, designed to delineate the temporal relationship between the inflammatory challenge (sponge implantation) and MAIF administration, was carried out. In this study, 20 mg of MAIF were administered intravenously 30, 60 or 120 minutes after sponge implantation. A fourth, control, group were left untreated. There were five animals in each group. Two sponges were implanted in each animal and these were removed after 24 hours. The results are illustrated in FIG. 22. Included on this graph are results obtained from a sample group of rats that received 20 mg of MAIF at the time of implantation (see FIG. 21).

Figure 23:
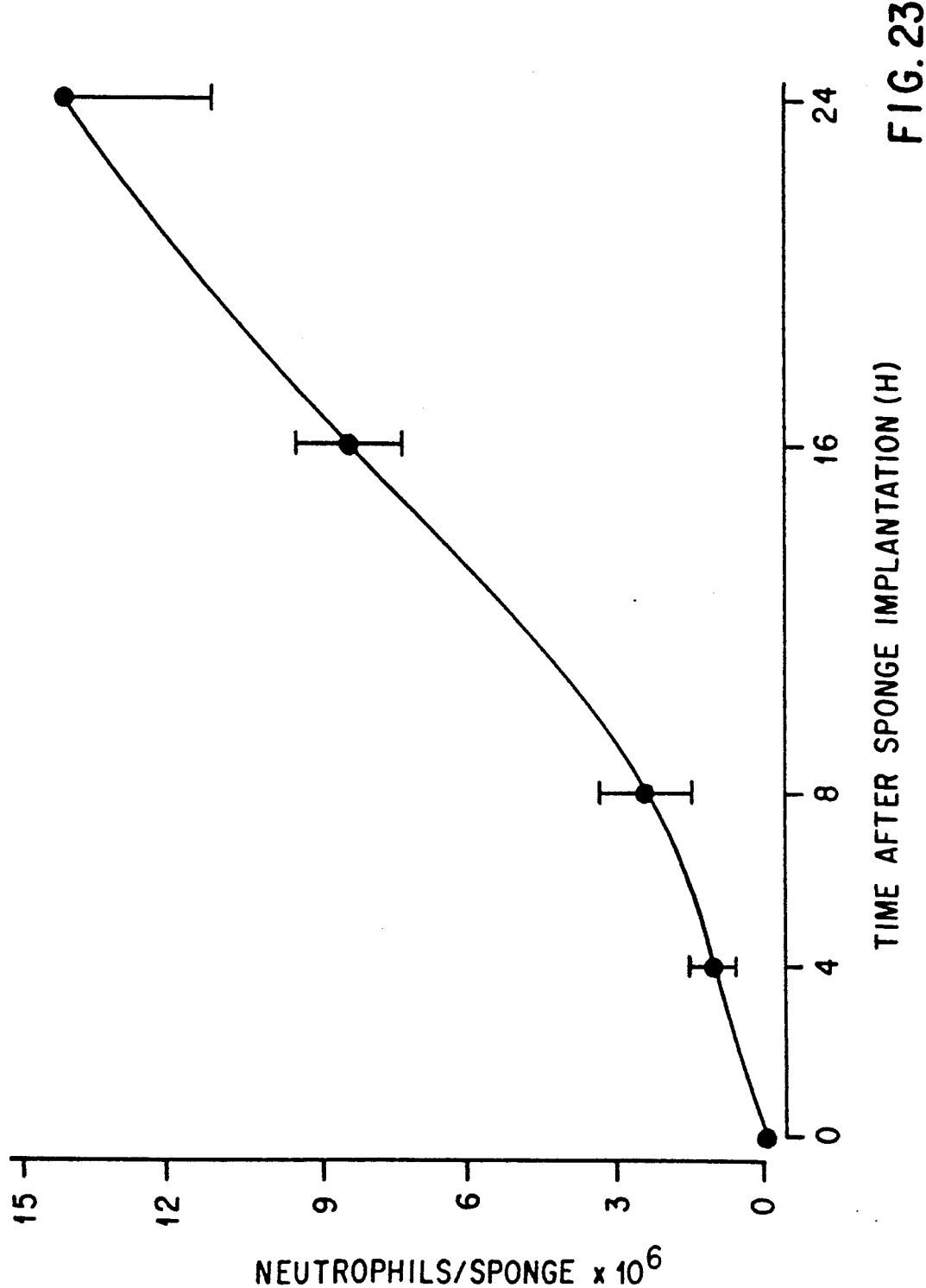
FIG. 23. Time course of the cellular inflammatory infiltration into subcutaneously implanted sponges in normal animals.

Results from the time-course of the effect of MAIF on carrageenan-induced footpad edema show MAIF to be comparatively ineffective when administered 60 minutes or later after challenge. It is noteworthy that while 20 mg of MAIF is required to suppress the inflammation associated with the sponge implantation, 4 mg is sufficient to inhibit the carrageenan-induced edema. Without intending to be held to this interpretation, this disparity may be related to the different level of provocation presented to the host by the two stimuli. The sponge implant is a relatively benign stimulus which induces a slow inflammatory response and the bulk of the cells accumulate between 8 and 16 hours after implantation (FIG. 23). On the other hand the subcutaneous injection of carrageenan is a very strong stimulant which induces a correspondingly strong response over a relatively short period (FIG. 16).

EXAMPLE 15

Effect of MAIF on Circulating Leucocytes

Several pharmacological agents can inhibit neutrophil migration. While some, such as cyclophosphamide, are cytoreductive and act by inhibiting hemopoiesis in the bone marrow, other agents, such as steroids and the non-steroidal anti-inflammatory drugs, have specific sites of action and do not result in leucocytosis. It was important therefore to determine the effect of MAIF on circulating white blood cell numbers and ratios.

Figure 24B:
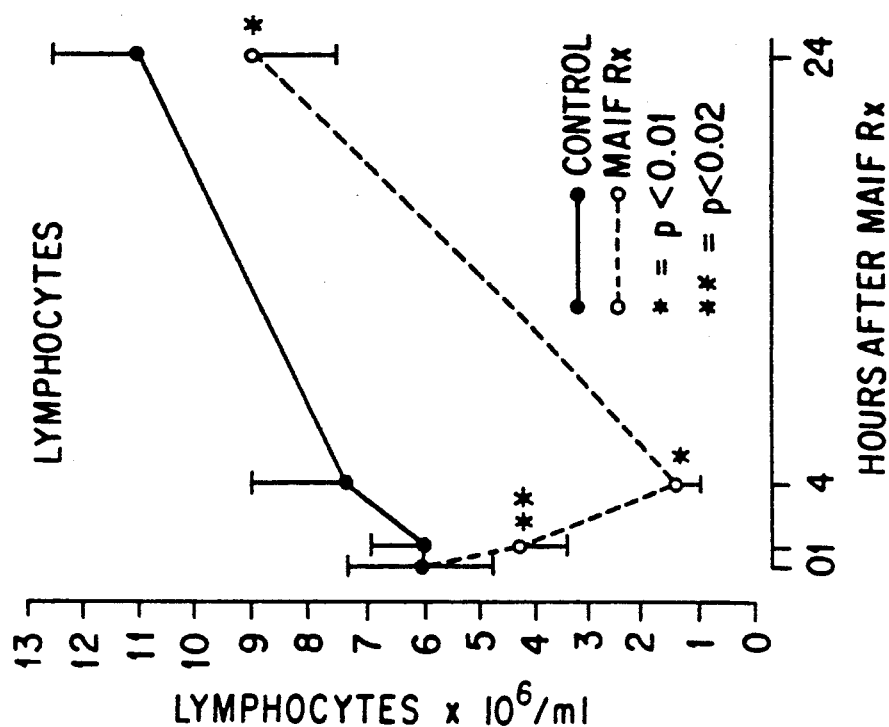
FIG. 24. Effect of 40 mg of MAIF administered i.v. on the number of circulating neutrophils and lymphocytes in the 24 hours following injection.
Figure 24A:
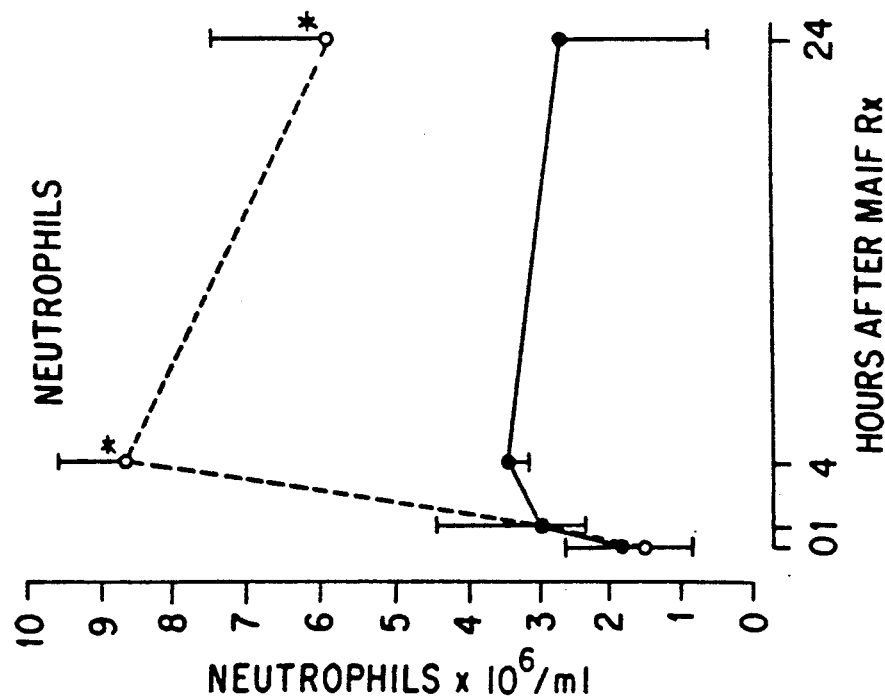

Two experiments were done. In the first, MAIF was administered intravenously at a dose of 40 mg/rat to one group of 6 animals and a control group was injected with saline. Blood samples were obtained at baseline, 1, 4, and 24 hours after treatment. The results are summarized in FIG. 24.

MAIF administration resulted in an increase in circulating neutrophil numbers, maximal at 4 hours, and a corresponding decrease in the number of peripheral blood lymphocytes. A further dose-response study was carried out in which a group of rats were injected intravenously with saline, 5, 10 or 20 mg of MAIF. Blood from each rat had been taken 7 previously to provide baseline values and was taken again 4 hours after the injection of MAIF. The results are shown in FIG. 25. Included on the graph are the results obtained from the sample taken 4 hours after the administration of 40 mg MAIF (see FIG. 24).

All doses of MAIF resulted in an increase in the number of circulating neutrophils and a decrease in the number of lymphocytes. While the effect on lymphocytes was linearly related to dose, the increase in neutrophil numbers was in the form of a curve, the greatest effect being observed in those animals given 10 mg.

These results support the concept that MAIF modulates inflammation by affecting the adhesion of neutrophils to endothelial cells.

Data were also obtained pertaining to the effect of three other cell-targeted, anti-inflammatory/immunomodulatory agents on circulating leucocytes in the rat. The steroidal drug, methylprednisolone, causes a change in the lymphocyte/neutrophil ratio analogous to that seen with MAIF. The temporal relationship between drug administration and effect is somewhat different. The anti-injection/anti-inflammatory agent cyclosporin A also causes an increase in the number of circulating neutrophils but lymphocyte numbers are either increased or not affected depending on the dose. In contrast, the cytotoxic drug cyclophosphamide depletes both circulating lymphocytes and neutrophils. The effects of MAIF would appear to closely parallel the action of methylprednisolone.

EXAMPLE 16

Suppression of Infection Induced Inflammation by MAIF

Experiments have been carried out to determine whether changes in serum levels of acute phase reactants (APRs) could be used to quantify the anti-inflammatory activity of MAIF. The APRs are a group of proteins which are synthesized in response to an inflammatory stimulus. One of these, alpha 2 macroglobulin, is common to both man and rats and methodology for measuring this inflammatory component is available. Two intravenous injections of MAIF (0 and 24 hours) did not reduce the peak response (48 hours) of alpha 2 macroglobulin. This result indicates that MAIF does not effect the later inflammatory response.

EXAMPLE 17

In Vitro and In Vivo Evaluation of Milk Derived Anti-Inflammatory Factor (Bovine Mammary Macrophage Assay, Infection Models in Mice)

Incubation of bovine mammary macrophages with the hyperimmune milk fraction (MAIF) did not detectably enhance the degree of phagocytosis but did increase the ability of macrophages to kill phagocytosed *Staphylococcus aureus*. Mice injected intraperitoneally with 10 mg MAIF per kilogram demonstrated increased resistance to intraperitoneal challenge with lethal *Staphylococcus aureus*.

In an anti-mammary *Staphyloccocus aureus* mastitis challenge model, MAIF injected mice also showed significantly less mammary inflammation and involution and increased clearance of the infectious organism. Quantitative histological analysis of mammary tissue from MAIF treated mice showed significantly more lumen, less interalveolar connective tissue, and less leukocytic infiltration compared to control mice. Mammary glands of treated mice also contained fewer colony forming units than control mice. MAIF appears to exert its effects on the non-specific defense system by a modulation of leukocyte function.

EXAMPLE 18

Effect of MAIF on the Pathogenesis of Experimental Infection

The most common inflammagens encountered by man are microbial and it is important to determine the effect of any agent which modulates host defenses against infection. The tissue damage which accompanies many infectious diseases is in fact caused by the host response to infection rather than by the invading organism. While the ability to modulate the inflammatory response to infection could be a useful clinical technique, it must be recognized that inhibition of the host response during infection can be disadvantageous. This is especially true in the case of neutrophil inhibition. Studies with agents which curb the participation of neutrophils in the early stages of infection have demonstrated that, while inflammation and tissue damage may be initially suppressed, the increased bacterial load that occurs as a result of the reduced cellular response eventual leads to an exacerbation of tissue damage. Thus, it is essential to evaluate the potential of MAIF to modulate infection in order to (1) determine if the agent can reduce infection-induced tissue damage and (2) to assess whether any observed suppression of the host response is accompanied by an increase in the severity of infection.

Figure 26:
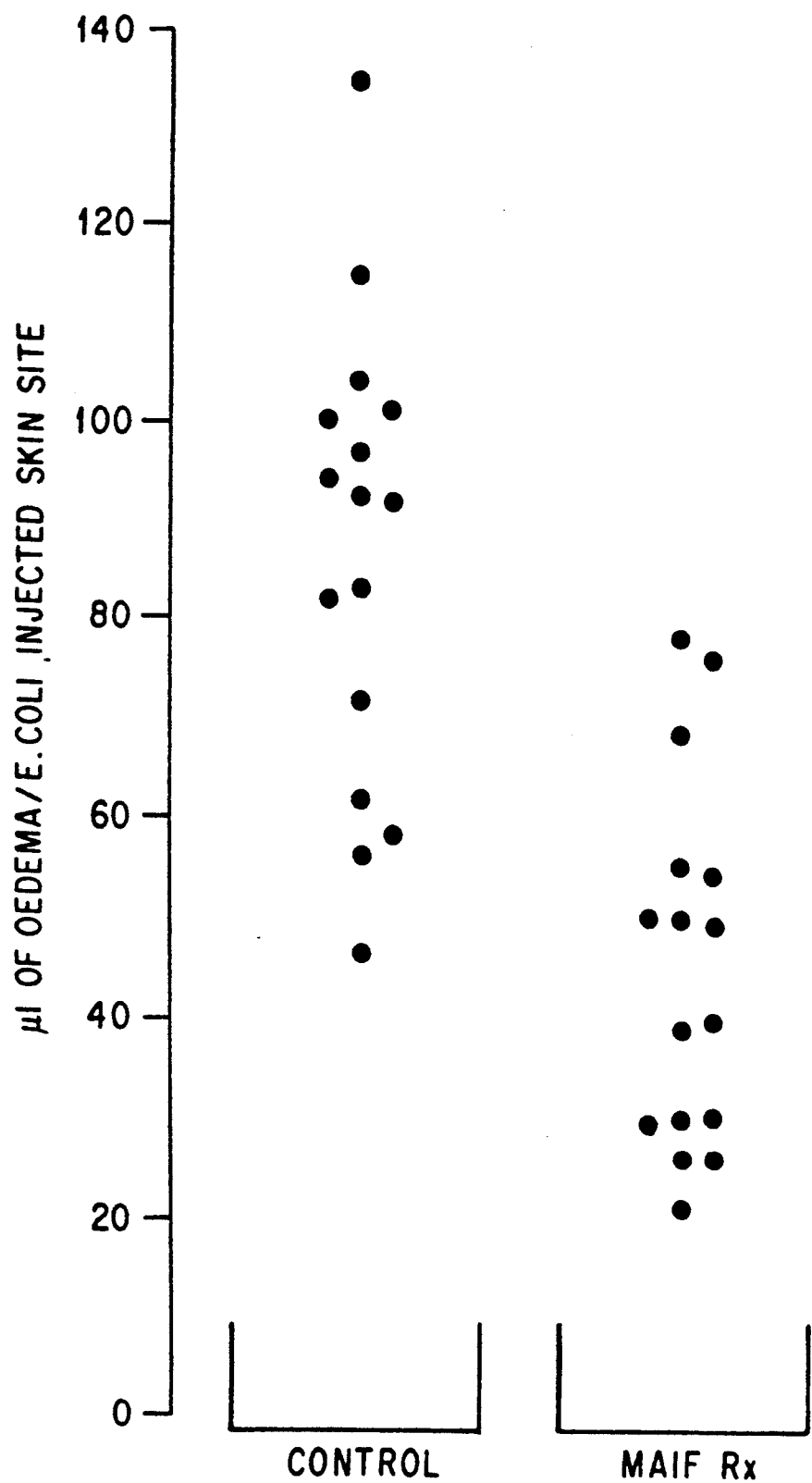
FIG. 26. Suppression of infection-induced edema by 40 mg of MAIF injected i.v. The mean values of the two groups were: controls, 87±22 μL; MAIF, 45±17 μL; p<0.01.

The effect of MAIF on edema formation following the intradermal injection of *E. coli* 075 was determined. Two groups of 8 animals were used. One group was untreated and served as controls while individuals in the second group were injected intravenously with 40 mg of MAIF in 0.5 ml saline. Immediately after the administration of MAIF, 100 µl of an overnight culture of *E. coli* 075 was injected intradermally at two skin sites on the shaved back of the rat, followed by the intradermal injection of 100 µl of saline at two further sites. To allow estimation of edema volume in the infected skin, 0.1 µCi of $^{125}$I-HSA was injected intravenously at the time of challenge. Six hours later the animals were anaesthetized, a blood sample obtained, the skin on the back removed and the infected and saline injected sites punched out. The volume of edema was calculated by relating tissue counts to plasma counts as described. To obtain the volume of edema which accumulates as a result of the presence of *E. coli* the edema/plasma volume of the saline-injected sites was subtracted. The results are shown in FIG. 26.

MAIF administration resulted in a 48% inhibition of edema formation. This experiment established that MAIF could modulate the local inflammatory response to infection.

Figure 27:
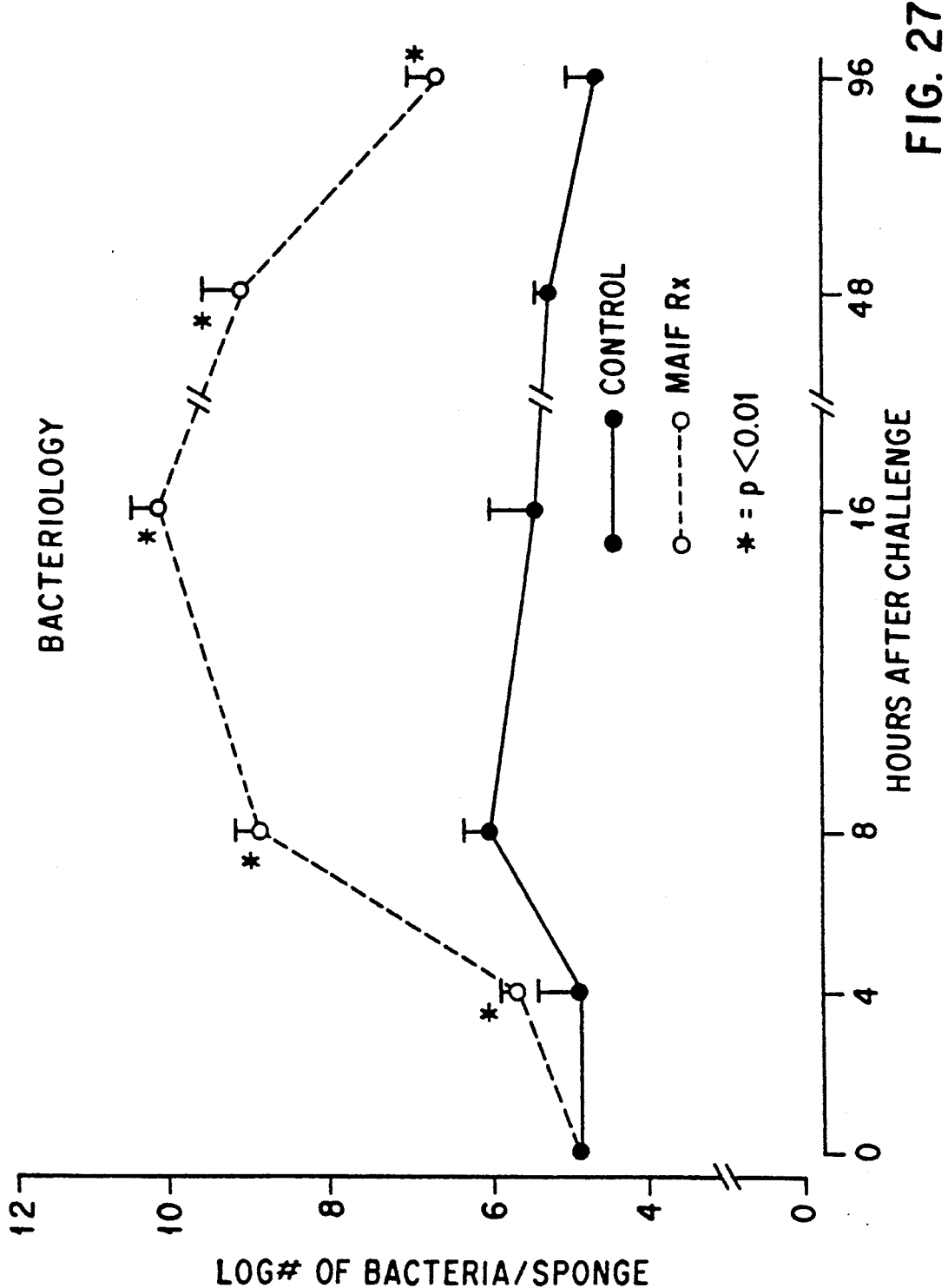
FIG. 27. Effect of MAIF given i.v. at 40 mg per rat on bacterial replication and subcutaneously implanted, E. coli-infected sponges.
Figure 28:
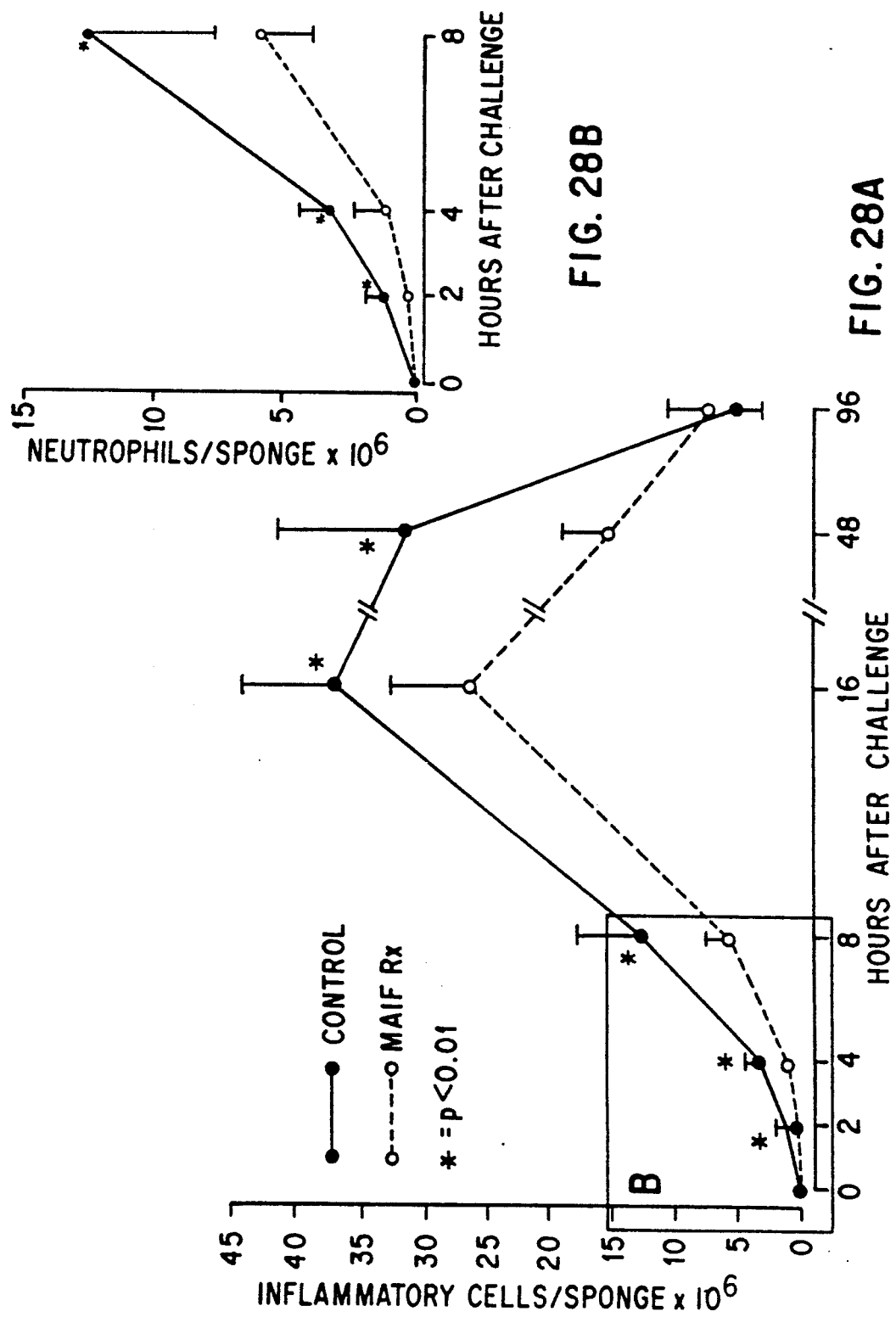
FIG. 28. Inhibition of inflammatory cell infiltration into infected sponges by MAIF (40 mg per rat, i.v.).
Figure 29:
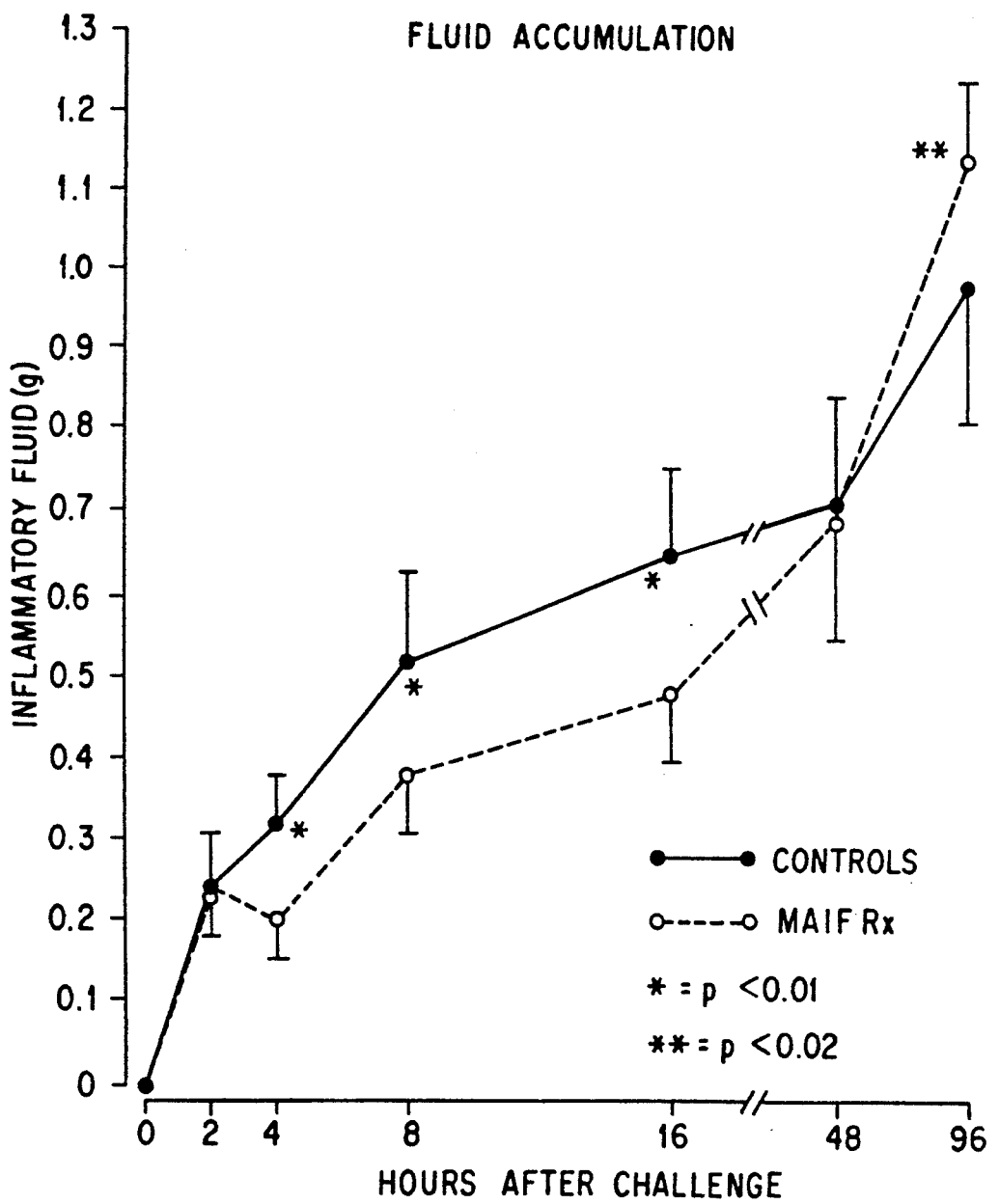
FIG. 29. Effect of MAIF (40 mg per rat, i.v.) on suppression of the intermediate phase (4-16 hours) of inflammatory fluid accumulation in E. coli-infected sponges.

In order to study the relationships between MAIF administration, bacterial replication, the accumulation of fluid and inflammatory cell infiltration, an alternative model of infection was employed. Polyurethane sponges, prepared and implanted as previously described, were infected with a quantitated sample of *E. coli* 075 at the time of implantation. The sponges were removed at timed intervals, weighed to determine the volume of the fluid exudate, and then squeezed in media to free the bacteria and cells from the sponge. Bacterial and cell numbers were estimated using techniques known to those skilled in the art. The following experiment was carried out using this model. Ninety animals were divided into two groups of 45. One of these groups was untreated and served as controls. The second group were injected intravenously with 40 mg of MAIF. The sponges were then implanted subcutaneously and, at the time of implantation, each sponge was inoculated with $10^5$ *E. coli* 075. Groups of 6-8 animals were killed at intervals thereafter and the bacteriological status and the size of the inflammatory infiltrate in the sponges determined. The results are illustrated in FIGS. 27-29.

The rate of bacterial replication was much greater in MAIF treated animals than in the controls and there was a 10, 1000 and 10,000 fold difference in bacterial numbers at 4, 8 and 16 hours respectively. Thereafter, bacterial numbers declined, although there was still a large difference at 96 hours (FIG. 27).

The early response to infection is the critical determinant in the outcome of an infectious episode. In this experiment the cellular infiltrate at 2, 4 and 8 h in those animals given MAIF was 27%, 35% and 46% of the control infiltrate respectively (FIG. 28B). The cells which accumulate in the first 24 h after challenge are >90% neutrophils and the suppression of this cellular component during this phase may account for the rapid increase in bacterial numbers. The accumulation of fluid at 2 hours was not affected by the administration of MAIF, but was significantly less 4, 8 and 16 hours following challenge. This is consistent with the previous finding that MAIF did not suppress the primary, non-cellular phase of edema formation in the carrageenan footpad model. In previous studies, using the immunomodulatory agents cyclosporin A and methylprednisolone, a similar association between the suppression of the acute cellular inflammatory infiltrate and the promotion of bacterial replication was shown. However, in these experiments, the increased bacterial load promoted a host response between 24 and 48 hours post challenge in which there was a massive influx of neutrophils. When tissue was involved, the enhanced inflammatory response resulted in a marked exacerbation of tissue damage and scar formation. Interestingly, although administration of MAIF suppressed the early inflammatory response and was associated with a 10,000 fold increase in bacterial numbers there was no massive influx of neutrophils 24-48 hours post challenge.

EXAMPLE 19

Effect of MAIF on Experimental Pyelonephritis

An agent which can suppress inflammation in infection without resulting in a sequela of enhanced tissue damage would have considerable potential. A clinically relevant model of infectious disease could provide an experimental basis for establishing such potential.

Pyelonephritis is an infectious disease which demonstrates local inflammation, tissue destruction and scar formation as cardinal histological features. A well characterized model of the disease is available, which reproduces the central pathological features of the disease in man. Pyelonephritis is induced in the rat by the direct inoculation of the surgically exposed kidney with a predetermined number of *E. coli* 075. Following challenge, bacterial numbers increase rapidly and reach a peak 3 to 4 days later. In normal animals the level of infection declines over the following 5 or 6 days and reaches a plateau at about 10 days post challenge. By 21 days the lesions have resolved and present as focal areas of indented scar tissue. To assess the effect of MAIF on this model of infection, pyelonephritis was induced in both kidneys of twenty-six animals. One half of these animals were treated with MAIF intravenously at a dose of 40 mg/rat at the time of challenge and again 48 hours later. Seven animals from each group were killed 4 days after induction of pyelonephritis and the two remaining groups of six animals at 21 days. Kidneys were removed aseptically and weighed to determine the relative volume of the fluid exudate. The extent of the of surface lesion size was estimated by direct visualization and the kidney homogenized to allow the enumeration of bacterial numbers. The results are shown in FIG. 30.

Four days after challenge the inflammatory response, as evidenced by the inhibition of fluid accumulation and the size of the lesions on the surface of the kidney, was suppressed by the administration of MAIF. As previously observed in the studies involving infected, subcutaneously implanted sponges, the early suppression of inflammation resulted in a logarithmic increase in the number of bacteria in MAIF-treated animals. By 21 days there was no difference in the pathology of disease as measured by kidney weight, bacterial numbers or renal surface lesions size. Thus, while suppression of the early inflammatory response with MAIF did not result in a reduction in tissue destruction in the chronic (21 day) phase of pyelonephritis, neither did it promote the development of pathological lesions as other anti-inflammatory and immunomodulatory agents have done.

EXAMPLE 20

Summary of Experimental Data

A method was developed which allowed the accumulation of edema in the carrageenan injected footpad to be monitored continuously.

The early, non-phagocytic, phase of the inflammatory response was not affected by MAIF, whereas the later, cellular-driven, phase of the reaction was significantly inhibited. Further experiments, in which MAIF was administered at intervals before or after the injection of carrageenan, provided additional evidence that MAIF exerted its anti-inflammatory effect by modulating the secondary, neutrophil-mediated, inflammatory response.

MAIF was shown to have a half-life of 1-2 hours following i.v. injection and development of inflammation could be suppressed when the agent was administered 30 minutes after challenge. This result is relevant to the potential therapeutic use of MAIF.

The neutrophil is the principal cell involved in the acute inflammatory response. During the Arthus reaction, a >80% reduction in neutrophil accumulation was observed following MAIF administration which, in turn, was associated with a highly significant inhibition of the secondary characteristics of the inflammatory reaction, namely edema and hemorrhage. This result further implicated neutrophils as a target in MAIF-induced suppression of inflammation.

One of the key steps in the development of inflammation is the migration of neutrophils from the vasculature to the tissue. The intravenous administration of MAIF was shown to result in profound and dose dependent inhibition of neutrophil migration. When the effect of MAIF on peripheral blood leucocytes was investigated, a marked increase in the number of circulating neutrophils was observed, accompanied by a corresponding decrease in the number of lymphocytes. This effect was also dose-dependent, but in the case of the increase in neutrophil numbers, was not linear.

Finally, the agent significantly suppressed the early cellular response to infection, an effect which resulted in a logarithmic increase in bacterial numbers in a model of subcutaneous infection. This exacerbation of infection did not result in a rebound of the inflammatory response, as seen with other agents which suppress acute inflammation in infection. A second experiment using a clinically relevant model of infection, pyelonephritis, also demonstrated a suppressive effect on inflammation which was associated with an increase in bacterial numbers. Again no rebound effect was observed and there was no difference in the degree of tissue damage which occurred in the MAIF treated and control groups.

The following conclusions can be drawn from this series of experiments:

1. MAIF, administered i.v., suppresses the secondary, neutrophil-mediated, phase of the carrageenan induced inflammatory response.
2. When evaluated in the carrageenan footpad assay MAIF has a biological half-life of 1-2 hours and is effective even when administered after inflammation is induced. Subsequent experiments indicate that the effective half-life is dependent on both the dose and inflammatory stimulus employed.
3. MAIF inhibits neutrophil emigration in vivo.
4. MAIF administration results in an increase in the number of circulating neutrophils and a corresponding decrease in lymphocyte numbers.
5. MAIF suppresses host defenses against infection, probably via an effect an neutrophil emigration.

The experimental data obtained in these studies demonstrate clearly that MAIF has a marked effect on the neutrophilic component of the inflammatory response. The effects we have observed to data may be the result of a direct effect of MAIF on neutrophils per se, or the result of the suppression (or stimulation) of some other cellular or soluble mediator which indirectly alters the neutrophilic response. It is also widely accepted that few pharmacological agents are monospecific in their actions and it is possible that MAIF will be found to affect a number of different biological processes.

Having now generally described this invention, it will become readily apparent to those skilled in the art that many changes and modifications can be made thereto without affecting the spirit or scope thereof.

What is new and claimed and intended to be covered by Letters Patent of the United States is:

1. An anti-inflammatory composition produced by a process comprising:
   (i) removing the fat from milk of a milk-producing animal to produce skimmed milk;
   (ii) pasteurizing said skimmed milk;
   (iii) removing casein from said pasteurized skimmed milk to produce whey;
   (iv) removing from said whey macromolecules having a molecular weight greater than about 10,000 daltons to produce a composition free of macromolecules having a molecular weight greater than about 10,000 daltons;
   (v) reducing the ionic strength of said composition of step (iv) to produce an aggregate with anti-inflammatory activity, said aggregate having a molecular weight greater than about 5,000 daltons;
   (vi) removing from said composition of step (v) macromolecules having a molecular weight less than about 5,000 daltons to produce a composition free of macromolecules having a molecular weight less than about 5,000 daltons;
   (vii) collecting said composition of step (vi).

2. The composition of claim 1 wherein said removing in step (vi) is by means of a membrane filter.

3. The composition of claim 2 wherein said membrane filter is an Amicon YM5 membrane filter.

4. A process for producing an anti-inflammatory composition, comprising:
   (i) removing the fat from milk of a milk-producing animal to produce skimmed milk;
   (ii) pasteurizing said skimmed milk;
   (iii) removing casein from said pasteurized skimmed milk to produce whey;
   (iv) removing from said whey carbomolecules having a molecular weight greater than about 10,000 daltons to produce a composition free of macromolecules having a molecular weight greater than about 10,000 daltons;
   (v) reducing the ionic strength of said composition of step (iv) to produce an aggregate with anti-inflammatory activity, wherein said aggregate has a molecular weight greater than about 5,000 daltons;
   (vi) removing from said composition of step (v) macromolecules having a molecular weight less than about 5,000 daltons to produce a composition free of macromolecules having a molecular weight less than about 5,000 daltons;
   (vi) collecting said composition of step (vi).

5. The process of claim 4 wherein said removing in step (vi) is by means of a membrane filter.

6. The process of claim 5 wherein said membrane filter is an Amicon YM5 membrane filter.

7. A method of inhibiting the cellular inflammatory response in a mammal wherein said method comprises administering a milk anti-inflammatory composition, produced by the process of claim 1, to said manual, in an amount sufficient to inhibit the cellular inflammatory response.

8. A method of inhibiting the Arthus reaction in a mammal wherein said method comprises administering a milk anti-inflammatory composition, produced by the process of claim 1, to said mammal, in an amount sufficient to inhibit said Arthus reaction.

9. A method of inhibiting the adhesion of neutrophils to endothelial cells in a mammal, wherein said method comprises administering a milk anti-inflammatory composition, produced by the process of claim 1, to said mammal, in an amount sufficient to inhibit said adhesion.

10. The method of claim 7, wherein said cellular inflammatory response is migration of inflammatory cells.

11. The method of claim 10, wherein said inflammatory cells are neutrophils.

12. The method of claim 7, wherein said cellular inflammatory response is the Arthus reaction.

13. The method of claim 7, wherein said cellular inflammatory response is the result of infection.

14. The method of claim 7, wherein said cellular inflammatory response is the result of acute phase reactants release.

15. A method of inhibiting cytokine action in a mammal wherein said method comprises administration of milk anti-inflammatory factor, produced by the process of claim 1, to said mammal, in an amount sufficient to inhibit said cytokine action.

16. The method of claim 15, wherein said cytokine action is at the receptor of an inflammatory cell.

17. The method of any one of claims 10–14, 15, 16, and 7–9 wherein said milk anti-inflammatory factor is administered intravenously.

18. The method of any one of claims 10–14, 15, 16, and 7–9 wherein said milk anti-inflammatory factor is administered orally.

19. The method of any one of claims 10–14, 15, 16, and 7–9 wherein said milk anti-inflammatory factor is administered intraperitoneally.

20. The method of any one of claims 10–14, 15, 16, and 7–9 wherein said milk anti-inflammatory factor is administered intramuscularly.

21. The method of any one of claims 15, 7, 8 and 9 wherein said milk anti-inflammatory factor is derived from a bovine.

22. The method of any one of claims 15, 7, 8 and 9, wherein said hyperimmunized milk anti-inflammatory factor is derived from an animal in a hyperimmunized state and said state is induced by administration of a polyvalent mixture of bacterial antigens comprising: *Stapholococcus aureus; Stapholoccocus epidermidis; Streptococcus pyogenes*, A Type 1; *Streptococcus pyogenes*, A. Type 3; *Streptococcus pyogenes*, A. Type 5; *Streptococcus pyogenes*, A. Type 8; *Streptococcus pyogrenes*, A. Type 12; *Streptococcus pyogenes*, A. Type 14; *Streptococcus pyogenes*, A Type 18; *Streptococcus pyogenes*, A. Type 22; *Aerobacter aerogenes; Escherichia coli, Psuedomonas aeruginosa; Klebsiella pneumoniae; Salmonella typhimurium; Haemophilus influenzae; Streptococcus mitis; Proteus vulgaris; Shigella dysenteriae; Diplococcus pneumoniae; Proprionibacter acnes* (anaerobe); *Streptococcus mutans*; or *Streptococcus agalactiae*.

23. The method of claim 22, wherein said polyvalent bacterial antigen is administered to said animal orally.

24. The method of claim 22, wherein said polyvalent vaccine is administered parenterally.

25. The method of any one of claims 15, 7, 8 and 9, wherein said inflammation is caused by a condition selected from a group consisting of acute and subacute bursitis, acute non-specific tendonitis, systemic lupus erythematosis, systemic dermatomyositis, actue rheumatic carditis, pemphigus, bullous dermatitis, herpeteformis, severe erythema, multiform exfoliative dermatitis, cirrhosis, seasonal perennial rhinitis, bronchial asthma, ectopic dermatitis, serum sickness, keratitis, opthalmicus iritis, diffuse ureitis, choriditis, optic neuritis, sympathetic opthalmia, symptomatic sarcoidosis, Loeffler's syndrome, berylliosis, and hemolytic anemia.

* * * * *